United States Patent [19]
Venter et al.

[11] Patent Number: 5,344,776
[45] Date of Patent: Sep. 6, 1994

[54] DNA ENCODING AN INSECT OCTOPAMINE RECEPTOR

[75] Inventors: John C. Venter; Claire M. Fraser; William R. McCombie, all of Silver Spring, Md.

[73] Assignee: The United States of America as represented by the Department of Health and Human Services, Washington, D.C.

[21] Appl. No.: 676,174

[22] Filed: Mar. 28, 1991

[51] Int. Cl.$^5$ .................. C12N 15/12; C12N 15/63
[52] U.S. Cl. .................... 435/252.3; 435/69.1; 435/320.1; 536/23.5
[58] Field of Search .................. 435/91, 171.2, 252.3, 435/7.1; 530/350; 935/11

[56] References Cited

PUBLICATIONS

Arakawa et al. Cloning Localization and Permanent Expression of a Drosophila Octopamine Receptor Mar., 1990. Neuron vol. 2 pp. 343–354.
Saudou et al. Cloning and characterization of a Drosophila tyramine receptor Nov., 1990 EMBO vol. 9 (11) pp. 3611–3617.

Primary Examiner—Robert J. Hill, Jr.
Assistant Examiner—John D. Ulm
Attorney, Agent, or Firm—National Institutes of Health Office of Technology Transfer

[57] ABSTRACT

The present invention pertains in general to invertebrate octopamine receptor proteins and to polynucleotides encoding such receptors. The present invention also relates to insect for example, Drosophila octopamine receptors that are recombinantly expressed in mammalian cells where the receptor mediates the attenuation of adenylate cyclase activity and exhibits a pharmacological profile that is unique but closely related to mammalian adrenergic receptors. The present invention further relates to drug screening methods for the development of specific human pharmacological drugs and insecticides targeted for the octopamine receptor system.

11 Claims, 19 Drawing Sheets

```
-318 GAATTCGTTCTTGTGTAATAAATAAATTGCCAACAATTATAACTTGCAGT
     CCACTCAGGCATATTCAAATGAAATGTGCCACAAAATGTT                    -229

-228 TACGGTCATTGCAACTCAAAGCGACAGACCATAGACGAGGTGCAAGGTGT
     TGTGGCAGTTGCAGAAAAACTAAAAGAAAGCCGTAAGGCT                    -139

-138 TGACCAAAAATTAATAACTGATAAAAGCAGAAATAAGTCAAAGAAGTCGG
     GGAAATCGCACTCAACGTCCGCCTTTCCACCAAGACGCAT                    -49

-48  GTAAACGCAACCGGAGCCCAAAGAAGGCAAGTGGCAGGGCAGGGAAA

MetProSerAlaAspGlnIleLeuPheValAsnValThrThr
     GATGCCATCGGCAGATCAGATCCTGTTTGTAAATGTCACCACA                   42

ThrValAlaAlaAlaAlaLeuThrAlaAlaAlaAlaValSerThrThr
 43  ACGGTGGCGGCGGCGGCTCTAACCGCTGCGGCCGCCGTCAGCACCACA

LysSerGlyAsnGlyAsnAlaAlaArgGlyTyrThrAspSer
     AAGTCCGGAAACGGCAACGCCGCACGGGGCTACACGGATTCG                   132
```

FIG. 1B

```
133  AspAspAspAlaGlyMetGlyThrGluAlaValAlaAlaAsnIle
     GATGACGATGCGGGCATGGGAACGGAGGCGGTGGCTAACATA                    222

223  SerGlySerLeuValGluGlyGlyGluThrThrValThrAlaAlaLeuSer
     TCCGGCTCGTGGTGGAGGGCCCTGACCACCGTTACCGGGCATTGAGT               312

313  ThrAlaGlnAlaAspLysAspSerAlaGlyGluCysGlyGlyAlaVal
     ACGGCTCAGGCGGACAAGGACTCAGCGGGAGAATGCGAAGGAGCTGTG

GluGluLeuHisAlaSerIleLeuGlyLeuGlnLeuAlaVal
     GAGGAGCTGCATGCCAGCATCCTGGGCCTCCAGCTGGCTGTG

403  ProGluTrpGluAlaGluThrAlaGluValAlaGluSerValIleIle
     CCGGAGTGGGAGGCCCTTCACCGCCCTGGTTCTCCTCGGTCATTATC                492

ValGluThrIleIleGlyAsnIleGlyValIleGluSerVal
     GTGCTGACCATCATCGGGAACATCCTGGTGATTCTGAGTGTG

493  PheThrTyrLysProLeuArgIleValGlnAsnPhePheIleValSer
     TTCACCTACAAGCCGCTGCGCATCGTCCAGAACTTCTTCATAGTTTCG               582

LeuAlaValAlaAspLeuThrValAlaLeuLeuValLeuPro
     CTGGCGGTGGCCGATCTCACGGTGGCCCTTCTGGTGCTGCCC

PheAsnValAlaTyrSerIleLeuGlyArgTrpGluPheGlyIleIleHis
     TTCAACGTCGCTTACTCGATCCTGGGGCGCTGGGAGTTCGGCATCCAC

LeuCysLysLeuTrpLeuThrCysAspValLeuCysCysThr
     CTGTGCAAGCTGTGGCTCACCTGCGACGTGCTGTGCTGCACT
```

FIG. IC

```
        SerSerIleLeuAsnLeuCysAlaIleAlaAlaLeuAspArgTyrTrpAla
583     AGCTCCATCCTGAACCCTGTGTGCCATAGCCCTGGACCGGTACTGGGC                672

IleThrAspProIleAsnTyrAlaGlnLysArgThrValGly
673     CATTACGGACCATCAACTATGCCCAGAAGAGACCGTTGGT                        762

ArgValLeuLeuLeuIleSerGlyValTrpLeuLeuSerLeuIle
763     CGCGTCCTGCTCCTCATCTCCGGGGTGTGGCTACTTTCGCTGCTGATA                852

SerSerProProLeuIleGlyTrpAsnAspTrpProAspGlu
853     AGTAGTCCGCCGTTGATCGGCTGGAACGACTGGCCGGACGAG                      942

PheThrSerAlaThrProCysGluLeuThrSerGlnArgGlyTyrVal
943     TTCACAAGCGCCACGCCCTGCGAGCTGACCTCGCAGCGAGGCTACGTG                1032
```

```
        IleTyrSerSerLeuGlySerPhePheIleProLeuAlaIle
        ATCTACTCCTCGCTGGGCTCCTTCTTTATTCCGCTGGCCATC

MetThrIleValTyrIleGluIleIlePheValAlaThrArgArgArgLeu
        ATGACGATCGTCTACATCGAGATCATTTCGTGGCCACGCGGCGGCCTA

ArgGluArgAlaArgAlaAsnLysLeuAsnThrIleAlaLeu
        AGGGAGCGAGCCAGGGCCAACAAGCTTAACACGATCGCTCTG

LysSerThrGluLeuGluProMetAlaAsnSerSerProValAlaAla
        AAGTCCACTGAGCTCGAGCCGATGGCAAACTCCTCGCCCGTGCCGCC

SerAsnSerGlySerLysSerArgLeuLeuAlaSerTrpLeu
        TCCAACTCCGGCTCCAAGTCGCGTCTCCTAGCCAGTGGCTT
```

FIG. 1D

```
1033  CysCysGlyArgAspArgAlaGlnPheAlaThrProMetIleGlnAsn
      TGCTGCGGGCCGGGATCGGGCCCAGTTCGCCACGCCTATGATCCAGAAC                    1122

1123  AspGlnGluSerIleSerSerGluThrHisGlnProGlnAsp
      GACCAGGAGAGCATCAGCAGTGAAACCCACCAGCCGCAGGAT                           1212

1213  SerSerLysAlaGlyProHisGlyAsnSerAspProGlnGlnHis
      TCCTCCAAAGCGGGTCCCCATGGCAACAGCGATCCCCAACAGCAGCAC                     1302

1303  ValValValLeuValLysLysSerArgArgAlaLysThrLys
      GTGGTCGTGCTGGTCAAGAAGTCGCGCGTGGCCAAGACCAAG                           1392

1393  AspSerIleLysHisGlyLysThrArgGlyGlyArgLysSerGlnSer
      GACTCCATTAAGCACGGCAAGACCCGTGGCCGCAAGTCGCAGTCC                        1482

1483  SerSerThrCysGluProHisGlyGluGlnHisLeuLeuPro
      TCGTCCACATGCGAGCCCCACGGCGAGCAACAGCTCTTACCC                           1572

AlaGlyAspGlyGlySerCysGlnProGlyGlyHisSerGly
      GCCGGGGACGGGGATGGGGCTAGCCCAGCCCGGGGAGGCCACTCTGGA

GlyGlyLysSerAspAlaGluIleSerThrGluSerGlySer
      GGCGGAAAGTCGGACGCCGAGATCAGCACGGAGAGCGGGAGC

AspProLysGlyCysIleGlnValCysValThrGlyAlaAspGluGly
      GATCCCAAAGGTTGCATACAGGTCTGCGTGACTCAGGCGGACGAGCAA

ThrSerLeuLysThrProProGlySerSerThrGlyVal
      ACGTCCCTAAAGACCCCGCCAATCCTCGACGGAGTC

AlaAlaValSerValThrProLeuGlnLysLysThrSerGlyValAsn
      GCTGCCGTTTCTGTCACTCCGTTGCAGAAGAAGACTAGTGGGTTAAC

GlnPheIleGluGluLysGlnLysIleSerGluLysGlu
      CAGTTCATTGAGGAGAAACAGAAGATCTCGCTTTCCAAGGAG
```

FIG. IE

```
           ArgArgAlaAlaArgThrLeuGlyIleIleuMetGlyIleValPheValGly
1573       CGGCGAGCGGCTCGCGACCCTGGGCATCATCATGGGCGTGTTCGTCATC       1662

CysTrpLeuProPhePheMetTyrValIleLeuProPhe
1663       TGCTGGCTGCCCTTCTTCATGTACGTCATTCTGCCCTTC                 1752

CysGlnThrCysCysProThrAsnLysPheLysAsnPheIleThrTrp
1753       TGCCAGACCTGCTGCCCCACGAACAAGTTCAAGAACTTCATCACCTGG        1842

LeuGlyTyrIleAsnSerGlyLeuAsnProValIleTyrThr
1843       CTGGGCTACATCAACTCGGGCCTGAATCCGGTCATCTACACC              1932

IlePheAsnLeuAspTyrArgArgAlaPheLysArgLeuLeuGlyLeu
1933       ATCTTCAACCTGGACTACCGCCGGGCCTTCAAGCGACTTCTGGGCCTG        2022

Asn
2023       AATTGAGGCTGGCTGGCCGGGGGGCGGGGTGGAAGATATAAACCG           2112

2113       GGCCAATCATGGTTCGAGCGGGAGAGCGTACCTCAAAGTTTGTGCCAA
           ACTTAAATGGTCGTGTATGCGTTCAGCGGAGATCTCAGTCTA              2202

2203       TGTACAGTTGGACCCCCAGTTGATGAACTTCCGAGTTCAACTTCTCTA
           ACACATATATACTTTCAAATGCCTTCTTGGTGAACTCATTTT

2293       GAAGAAGTGGATGAATTTGGTAAAGTGTAATAGATTGAATATAATTTT
           TAATGTTTAACGTTTCGGCAAAAGTGAAAAGCCCCACATTGG

2383       AAAGTCAAAGATGAGACTCGAGTGTATATATAGTTCAAACTAAGTTA
           TTATTTCTAGCCGTAATTAAAATACTTTCATTTTAGTTTTGAA
```

FIG. 1F

```
2203 CATTTTTTAATATATATTGTTGTTGTTTGGAATCGATTGAGATGTACCACCA
     CATTAAGCGTAGATTGTTCAATACTCATACTAAATGGGTTG              2292

2293 TGCTGCGATTAAAGTGAGGATGTTGCCTCAAGGCACAGCTACTAGGAA
     AATCATAAAAATTACATGGTAAAGAATTATACATGCATTATA              2382

2383 CTCCAGCTAAGTGGCATCCCAAACGAGAATAGCATCAAATTGAATTTA
     ATACAATTAAATTAAATGTTTAGGCACAAAGAATTGTGGCAA              2472

2473 CTTTCGTGTTTCACCCTAAGCGTATGGATAACCAAAAAGGTGTTTGTT
     AAATTAAATCTGCGCTCAAGATATGTAAGCAACTACTAAGCT              2562

2563 AAATAATAACTTCCAAGAGAGAAACGTTTTCTAGGCATTACTTTAACG
     ATTTGTATTTATATGTACTTTAATTGTTAGGTAAACGATAAAC              2652

2653 CACTATACCTAATGTATACTTTCAAATACGCTTTGGACTATTGTTAA
     ATAATTAACGATTAATTGTTTTTTATGGCATAGCAACTATTG              2742

2743 TGTTGAGTGGGCAGCTTAAAGCTAGCACATCGAAACTTACTTAAGGTA
     GATAAATGTTTAACTGCACGTTACGAAATGCAACAGAGTTGG              2832

2833 CGAAAGGACGTAATTCAATGGATGTGTTAACTCAAGTACATGCTATAT
     CGRAAATGTATATCACAATTTATGTCTTTTAACGACGATGTA              2922

2923 CGATAGTTTCACTAATTATATATTGTTTAACGAGAAAGAGCGAGCAAAGC
     GTAAATGAAACAAATAAAAGACACATTCGAATTAAAGTTAGG              3012

3013 AATTC                                                    3017
```

FIG. 3A

```
          1                                            *                                      50
OCTDRS    ............mp sadqilfvnv tttvaaaalt aaaavsttks gngnaargyt
A1HAM     .......... .......... .......... .......... ..........
A2BHUM    .......... .......... .......... ...maspala aaalavaaaag pnasgagerg
B1HUM     .......... .......... .......... .......... ....m..... gagvlvlgas
B1TUR     .......... .......... .......... .......... .......... .mgdgwlppd
B2HAM     .......... .......... .......... .......... .......... ..........
B2RAT     .......... .......... .......... .......... .......... ..........
D2RAT     .......... .......... .......... lfrtvttstt tttttttstt tttaspagys
M2RAT     .......... .......... .......... .......... .......... ..........
MDRS      mepvmslala ahgppsilep .......... .......... .......... ......mvn
S1CRAT    .......... .......... .......... .......... .......... ..........

Consensus ---------- ---------- ---------- ---------- ---------- ----------

51                                           *                                     100
OCTDRS    dsdddagmgt eavanisgsl vegltvtaa lstagadkds agecegavee
A1HAM     .......... .mnpdldtgh ntsapaqwge lkdanftgpn qtssnstlpq
A2BHUM    sggvanasga swgpprgqys agav...... .......... ..........
B1HUM     epgnlssaap lpdgaataar llvpasppas llppase... .......... 
B1TUR     cgphnrsggg gataaptgsr qv........ .......... ..........
B2HAM     .......... .......... .......... ....mgppgn dsdflittng
B2RAT     .......... .......... .......... ....mephgn dsdfllapng
D2RAT     .......... .......... .......... ...mdplnls wyddlerqn
M2RAT     .......... .......... .......... .......... ...mnnstn
MDRS      pgypgttllt alfenltsta asglydpysg mygngtngti qfetkgprys
S1CRAT    lgnavrsllm hligllvwqf disispvaai vtdtfnssdg grlfq.....

Consensus ---------- ---------- ---------- ---------- ----------
```

FIG. 3B

Transmembrane I

```
         101                                                                    150
OCTDRS   lhasilglql avpeweallt alvlsviivl tIiGNilvil Svftykplri
A1HAM    ldvt...... .......... raisv glvlgafilf aIvGNILvil Svacnrhlrt
A2BHUM   .......... .......... .....agl aavvgflivf tVvGNVLVvi AvltsraLra
A2HUM    aratpyslqv .......... ....tltl vclagllmll tVfGNVLVii AvftsraLka
B1HUM    .......spe plsqqwtagm gllmalivll iVaGNVLViv Alaktprlqt
B1TUR    .......sae llsqqweagm sllmalvvll iVaGNVLVia Algrtqrlqt
B2HAM    shvpdhdvte erdeawvvgm ailmsvivla iVfGNVLVit Alakferlqt
B2RAT    srapghditq erdeawvvgm ailmsvivla iVfGNVLVit Alakferlqt
D2RAT    wsrpfngseg kadrphynyy amltllifi iVfGNVLVcm Avsrekalqt
M2RAT    ssnnglaits pyktfevvfl vlvagsislv tIiGNILVmv Sikvsrhlqt
MDRS     las....... .......mvvm gfvaailstv tVaGNVMVmi Sfkidkqlqt
S1CRAT   .......... .fpdgvqnwp alsivviim tIgGNILVim Avsmekklhn Consensus -------- ---------- ---------- -V-GNVLV-- A------L--
```

Transmembrane II

```
         151                                                                    200
OCTDRS   vgNffIvsLA vADltVAllv Lp.fnvaysi lgrWefGihl CklWlTcDvL
A1HAM    ptNyfIvnLa iADlltSftv Lp.fsatIev lgyWvlGrif CdiWaAvDvL
A2BHUM   pqNlfLvsLA sADilVAtlv Mp.fslanel mayWyfGqvw CgvYlAlDvL
A2HUM    pqNlfLvsLA saDilVAtlv Ip.fslanev mgyWyfGktw CeiYLAlDvL
B1HUM    ltNlfImsLA sADivMGllv Vp.fgativv wgrWeyGsff CelWtSvDvL
B1TUR    ltNlfItsLA caDivMgllv Vp.fgativv rgtWlwGsfl CecWtSlDvL
B2HAM    vtNyfIsLA  cADlvMGlav Vp.fgashil mkmWnfGnfw CefWtSiDvL
B2RAT    vtNyfItsLA cADlvMGlav Vp.fgashil mkmWnfGnfw CefWtSiDvL
D2RAT    ttNylIvsLA vADlIVAtlv Mp.wvvylev vgeWkfSrih CdiFvTlDvM
M2RAT    vnNyfLfsLA cADliGvfs  Mnlytlytv. igyWplGpvv CdIWlAlDyV
MDRS     isNyfLfsLA iADfaIGais Mplfavtti. lgyWplGpiv CdtWlAlDyL
S1CRAT   atNyfLmsLA iADmlVGllv Mpllaily   dyvWplPryl CpvWiSlDvL Consensus --N---I--LA -AD--VG--- -M-------- ---W---G--- C--W---D-L
```

FIG. 3C

```
                Transmembrane III                                  Transmem-
         201                                                             250
OCTDRS   cctsSIInLc aIAldDRYwaI tdPinyaqkr Tvgrvlllis gvwLlsllis
A1HAM    cctASIlsLc aISiDRYigV ryslqyptlv Trrkailall svwvLstvis
A2BHUM   fctSSIvhLc aISlDRYwsV tgAveynlkr Tprrvkatlv avwIIsavis
A2HUM    fctSSIvhLc aISlDRYwsI tqAieynlkr Tprrikaili tvwvIsavis
B1HUM    cvtASIetLc vIAldDRYlaI tsPfryqsll Trarargvlc tvwaIsalvs
B1TUR    cvtASIetLc vIAidDRYlaI tsPfryqslm Trarakvilc tvwaIsalvs
B2HAM    cvtASIetLc vIAvDRYlaI tsPfkvqsll Tknkarmvll mvwiVsqIts
B2RAT    cvtASIetLc vIAvDRYvaI tsPfkyqsll Tknkarvvll mvwiVsgits
D2RAT    mctASIInLc aISiDRYtaV amPmlyntry Sskrrvtvmi aivwVlsfti
M2RAT    vsnASVmnLl iIsfDRYfcV tkPltypvkr Ttkmaqmmia aawvLsfilw
MDRS     asnASVlnLl iIsfDRYfsV trPltyrakr Ttnraavmig aawgIsillw
S1CRAT   fstASImhLc aISlDRYvaI rnPiehsrfn Srtkaimkla ivwaIsigvs Consensus ---ASI--L- -IS-DRY--I ---P------ T--------- ----I----- brane IV                         T r a n s m e m -
         251
OCTDRS   sppligwndw .pdeftsa.. ........tpc eltsQrgyvi ysslgSFFiP
A1HAM    igpllgwkep apndd..... ........kec gvteEpfyal fSSlgSFYiP
A2BHUM   fpplvslyrq ........ .pdgaaypqc glndEtwyil sSCiqsSFFaP
A2HUM    fpplisiekk ggg....... ggpqpaeprc eindQkwyvi aScigsFFaP
B1HUM    flpilmhwwr a....esdea rrcyndpkcc dfvtNrayai aSsvvSFYvP
B1TUR    flpimmhwwr ....dedpqa lkcyqdpgcc dfvtNrayai aSsiiSFYiP
B2HAM    fipiqmhwyr athqkaidcy ...hketcc dfftNqayai aSSivSFYvP
B2RAT    flpiqmhwyr athkqaidcy a....ketcc dfftNqayai aSSivSFYvP
D2RAT    scplifqlnn tdqne..... ........ ciianPafvv ySSivSFYvP
M2RAT    apailfwqfi ....... vgv rtvedgecyi qffsNaavtf gTaiaAFY1P
MDRS     ppwiyswpyi e........ gkr tvpkdecyiq fietNqyitf gTalaAFyfP
S1CRAT   vpipviglrd e........ ....skvfvnntt cvlnDpnfvl iGsfvAFFiP Consensus ---------- ---------- ----N----- -S---SFY-P
```

FIG. 3D

```
                    brane V
           301                                                              350
OCTDRS     laImtivYie ifvatrrrlr era.......... .......... ..........
A1HAM      laVilvmYcr vyivakrttk nleag....... .......... ..........
A2BHUM     cIImglvYar iyrvakrrtr .......... .......... ..........
A2HUM      cIImilvYvr iyqiakrrtr vpp....... .......... ..........
B1HUM      icImafvYlr vfreaqkqvk .......... .......... ..........
B1TUR      llImifvYlr vyreakeqir .......... .......... ..........
B2HAM      lvVmvfvYsr vfqvakr... .......... .......... ..........
B2RAT      lvVmvfvYsr vfqvakr... .......... .......... ..........
D2RAT      fiVtilvYik iyivlrkrrk .......... .......... ..........
M2RAT      vilmtvlywh israsksrik kekk...... .......... ..........
MDRS       vtImcflYwr iwretkkrqk dlpnlqagkk dsskrsnssd entvvnhasg
S1CRAT     ltImvityfl tiyvlrrqtl mllrg..... .......... ..........

Consensus  ---------- -----Y---- ---------- ---------- ----------

351                                                              400
OCTDRS     .......... .......... .......... .......... ..........
A1HAM      .......... .......... .......... .......... ..........
A2BHUM     .......... .......... .......... .......... ..........
A2HUM      .......... .......... .......... .......... ..........
B1HUM      .......... .......... .......... .......... ..........
B1TUR      .......... .......... .......... .......... ..........
B2HAM      .......... .......... .......... .......... ..........
B2RAT      .......... .......... .......... .......... ..........
D2RAT      .......... .......... .......... .......... ..........
M2RAT      .......... .......... .......... .......... ..........
MDRS       gllafaqvgg ndhdtwrrpr sessadaesv ymtnmvidsg yhgmhsrkss
S1CRAT     .......... .......... .......... .......... ..........

Consensus  ---------- ---------- ---------- ---------- ----------
```

FIG. 3E

```
            401                                              450
OCTDRS      ..........  ..........  ..........  ..........  ..........
A1HAM       ..........  ..........  ..........  ..........  ..........
A2BHUM      ..........  ..........  ..........  ..........  ..........
A2HUM       ..........  ..........  ..........  ..........  ..........
B1HUM       ..........  ..........  ..........  ..........  ....kidsce
B1TUR       ..........  ..........  ..........  ..........  ....kidrce
B2HAM       ..........  ..........  ..........  ..........  ..........
B2RAT       ..........  ..........  ..........  ..........  ..........
D2RAT       ..........  ..........  ..........  ..........  ..........
M2RAT       ..........  ..........  ..........  ..........  ..........
MDRS        ikstntikks  ytcfgsikew  ciawwhsgre  dsddfayeqe  epsdlgctsm
S1CRAT      ..........  ..........  ..........  ..........  ..........

Consensus   ----------  ----------  ----------  ----------  ----------

451                            *                 500
OCTDRS      ..........  ..ranklnt   ialkstelep  mansspvaas  nsgsksrlla
A1HAM       ......vm    kemsnskelt  lrihsknfhe  dt........  ..........
A2BHUM      ..........  ..........  .........t  lsekrapvgp  dg........
A2HUM       ..........  .srrgpdava  appggterrp  nglgpersag  pggaeaeplp
B1HUM       rrflggparp  pspspspvpa  papppgpprp  aa........  ..........
B1TUR       grfygsqeqp  qppp......  ..........  ..........  ..........
B2HAM       ..........  ........ql  qkidksegrf  hs........  ..........
B2RAT       ..........  ........ql  qkidksegrf  ha........  ..........
D2RAT       ..........  ..........  ..........  ep vangdpvsps  ..........
M2RAT       ..........  .gsvsavrpps illsdvsptp  lprpplasis  qlqemsavta
MDRS        nvmrdnysmg  ..........  ..........  ..rv        ntkrssrafr lvqgr.....
S1CRAT      ...hteeel   anmslnflnc  cckknggeee  na........  ..........

Consensus   ----------  ----------  ----------  ----------  ----------
```

FIG. 3F

```
         501                                                    550
OCTDRS   swlccgrdra gfatpmiqnd qesissethq pqdsskagp.  ..........
A1HAM    .......... .......... .......... .......... ..........
A2BHUM   .......... ..asptteng lgaaageart gtarprppt.  ..........
A2HUM    tqlngapgep apagprdtda ldleesss..  ..........  ..........
B1HUM    .......... .......... .......... .......... ..........
B1TUR    .......... .......... .......... .......... ..........
B2HAM    .......... .......... .......... .......... ..........
B2RAT    .......... .......... .......... .......... ..........
D2RAT    anlktplkda arrageleme mlsstapper tryspipps.  ..........
M2RAT    .......... ..ivkpn    nnnmpg....  ..........  ..........
MDRS     sttanvntag ngngainnnn nashngngav ngngagngag iglgttgnat
S1CRAT   .......... .......... .......... .......... ..........

Consensus  ---------- ---------- ---------- ---------- ----------

551                                                    600
OCTDRS   .......... .......... .......... .......... ..........
A1HAM    .......... .......... .......... .......... ..........
A2BHUM   .......... ...hqnsdpq qqhvvvlvkk srraktkdsi khqktrggrk
A2HUM    .......... .......... .......... .wartraaqr ..........
B1HUM    .......... .......... .......... ..sd       haerppgprr
B1TUR    .......... .......... .......... .......... ..........
B2HAM    .......... .......... .......... .......... ..........
B2RAT    .......... .......... .......... .......... ..........
D2RAT    .......... .......... .......... .......... ..........
M2RAT    .......... .gdgg      lehnkiqngk aprdgvtetc vqgeekessn
MDRS     hrdsrtlpvi nrinsrsvsq dsvytilirl psdgassnaa nggggppgag
S1CRAT   .......... .......... .......... .......... ..........

Consensus  ---------- ---------- ---------- ---------- ----------
```

FIG. 3G

```
         601                                                           650
OCTDRS   sqssstceph ge........ ..........  qqllpaggdg gscqpggghs gggksdaeis
A1HAM    .......... .......... .......... .......... .......... ..........
A2BHUM   prgga..... .......... .......... ....pgplrr ggrragaeg gaggadgqga
A2HUM    pergprgkgk arasqvkpgd .......... slrgagrgrr gsgrrlqgrg rsasglprrr
B1HUM    .......... .......... .......... .......... .......... ..........
B1TUR    .......... .......... .......... .......... .......... ..........
B2RAT    .......... .......... .......... .......... .......... ..........
D2RAT    .......... .......... .........h hqltlpdpsh hglhsnpdsp
M2RAT    dstssaavas nnrddeitqd entvstsldh srddnskqtc ikivtkaqkg
MDRS     aaasaslsmq gdcapsikmi hedqptttaa aa..plasaa atrrplpsrd
S1CRAT   .......... .......... .......... .......... .......... ..........

Consensus ---------- ---------- ---------- ---------- ---------- ----------

651                                                           700
OCTDRS   tesgadpkgc iqvcvt..qa deqtslkltp pqsstgvaav svtplqkkts
A1HAM    .......... .......... .......... .......... ..lsstkakg
A2BHUM   gpgaaqsga. .......... .......... ltasrspgpg grlsrassrs vefflsrrrr
A2HUM    agaqgq.... .......... .......... .......... .......... ..........
B1HUM    .......... .......... .......... .......... .......... .lpqhqpilg
B1TUR    .......... .......... .......... .......... .......... .pnlgqveqd
B2RAT    .......... .......... .......... .......... .......... .qnlsqveqd
D2RAT    akpeknghak ivnpriakff eigt...mpn gktrtslktm s......... elqnvvarki
M2RAT    dvytptsttv elv....... .......... ..gssgqsqd
MDRS     sefslplgrr mshaqhdarl lnakvipkql qkaggaagg gvggahalmn
S1CRAT   .......... .......... .......... .......... ........p npnpdqkprr Consensus ---------- ---------- ---------- ---------- ---------- ----------
```

FIG. 3H

```
                                                    Transmembrane VI
            701                                                                      750
OCTDRS   qvnqfieekq kislskErRa artLgilmgv FvIcWlPFfl myvilpfc.q
A1HAM    hnprssiavk lfkfsrEkKa aktLgiVvgm FiLcWlPFfi alplgslfst
A2BHUM   a..rssvcrr kvaqarEkRf tfvLavVmgv FvLcWfPFff iyslygicr.
A2HUM    .......... ....nrEkRf tfvLavVigv FvVcWfPFff tytltavgc.
B1HUM    ngragkrrps rlvaleEqKa lktLgilmgv FtLcWlPFfl anvvkafh..
B1TUR    ngraskrkts rvmamrEhKa lktLqilmgv FtLcWlPFfi vnivnvfn..
B2HAM    grsghglrrs skfclkEhKa lktLqiImgt FtLcWlPFfi vnivhviq..
B2RAT    grsghglrss skfclkEhKa lktLgiImgt FtLcWlPFfi vnivhvir..
D2RAT    ......rr klsqqkEkKa tqmLaiVlgv FiIcWlPFFi thilnihc..
M2RAT    vkmpkqpakk kpppsrEkKv trtIlaFlla FiItWaPYnv mvlintfc..
MDRS     arnaakkkkk sqekrqEsKa aktLsaIlls FiItWtPYni lvlikplt..
S1CRAT   kkkekrprgt mqainnEkKa skvLgiVffv FlImWcPFfi tnilsvlc..

Consensus ---------- ---------- ---------- ------E-K- ----L----I---- F-L-W-PF-- ----------

Transmembrane VII
            751                                                                      800
OCTDRS   tccp...... .......... ..thkfknfi twlgYInSgl NPviYtlfnl
A1HAM    lkp....... .......... ..pdavfkvv twlgYfnScl NPilYpcssk
A2BHUM   .......... ........eac qvpgplfkff fwigYcnSsI NPvlYtvfnq
A2HUM    .......... .......... svprtlfkff fwfgYcnSsl NPviYtlfnh
B1HUM    .......... .........re lvpdrlfvff nwlgYanSaf NPilY.crsp
B1TUR    .......... .........rd lvpdwlfvff nwlgYanSaf NPliY.crsp
B2HAM    .......... .........dn lipkevyill nwlgYvnSaf NPiiY.crsp
B2RAT    .......... .........an lipkevyill nwlgYvnSaf NPiiY.crsp
D2RAT    .......... .........dc nippvlysaf twlgYvnSav NPiiYttfni
M2RAT    .......... ........ap cipntvwtig ywlcYinSti NPacYalcna
MDRS     .......... .......tcsd ciptelwdff yalcYinSti NPmcYalcna
S1CRAT   .......... .....gkacnq klmekllnvf vwigYvcSqi NPivYtlfnk Consensus ---------- ---------- ---------- ----Y---S-- NP---Y----
```

FIG. 3I

```
          801
OCTDRS    dYRrAFkrlL  gln.......  ..........  ..........  ..........  ..........
A1HAM     eFKrAFmriL  gcqcrsgrrr  rrrrrlgaca  ytyrpwtrgg  slersqsrkd
A2BHUM    dFRaSFkhiL  frrrrrgfrq  ..........  ..........  ..........
A2HUM     dFRrAFkkiL  crgdrkriv.  ..........  ..........  ..........
B1HUM     dFRkAFgclL  ccarraarrr  hathgdrpra  sgclarpcpp  pspcaasddd
B1TUR     dFRkAFkrlL  cfprkadrrl  haggqpaplp  ggfistlgsp  ehspgtwsd
B2HAM     dFRiAFqelL  clrrssskay  gngyssnsng  ktdymgeasg  cqlgqekese
B2RAT     dFRiAFqelL  clrrssskty  gngyssnsng  rtdytgeqsa  yqlgqekene
D2RAT     eFRkAFmkiL  hc........  r.........  ..........  ..........
M2RAT     tFKkTFkhlL  schyknigat  ..........  ..........  ..........
MDRS      tFRrTYvriL  tckwhtrnre  gmvrqvyn..  ..........  ..........
S1CRAT    iYRrAFskyL  rcdykpdkkp  pvrqiprva.  ..........  ..........

Consensus -FR-AF---L  ..........  ..........  ..........  ..........

851                                                                 900
OCTDRS    ..........  ..........  ..........  ..........  ..........
A1HAM     slddsgscms  gsqrtlpsas  pspgylgrga  qpplelcayp  ewksgallsl
A2BHUM    ..........  ..........  ..........  ..........  ..........
A2HUM     ..........  ..........  ..........  ..........  ..........
B1HUM     dddvvcatpp  arllepwa..  ..........  gcngcaaads  dssldepcrp
B1TUR     cnggtrggse  ssleerhskt  srseskmere  knilattrfy  ctflgngdka
B2HAM     rlc.......  edppgtesfv  ncqgtvpsls  ldsqgrncst  ndspl.....
B2RAT     llc.......  eeapgmegfv  ncqgtvpsls  idsqgrncnt  ndspl.....
D2RAT     ..........  ..........  ..........  ..........  ..........
M2RAT     ..........  ..........  ..........  ..........  ..........
MDRS      ..........  ..........  ..........  ..........  ..........
S1CRAT    ..atalsgre  invniyrhtn  ervarkandp  epgiemqven  lelpvnpsnv Consensus ..........  ..........  ..........  ..........  ..........
```

FIG. 3J

|          | 901        |            |            |            |            | 950 |
|----------|------------|------------|------------|------------|------------|-----|
| OCTDRS   | .......... | .......... | .......... | .......... | .......... |     |
| A1HAM    | peppgprrgrl | dsgplftfkl | lgepespgte | gdasnggcda | ttdlangqpg |     |
| A2BHUM   | .......... | .......... | .......... | .......... | .......... |     |
| A2HUM    | .......... | .......... | .......... | .......... | .......... |     |
| B1HUM    | gfaseskv.. | .......... | .......... | .......... | .......... |     |
| B1TUR    | vfctvlrivk | lfedatctcp | hthlklmkwr | fkqhga.... | .......... |     |
| B2HAM    | .......... | .......... | .......... | .......... | .......... |     |
| B2RAT    | .......... | .......... | .......... | .......... | .......... |     |
| D2RAT    | .......... | .......... | .......... | .......... | .......... |     |
| M2RAT    | .......... | .......... | .......... | .......... | .......... |     |
| MDRS     | .......... | .......... | .......... | .......... | .......... |     |
| S1CRAT   | vserissv.. | .......... | .......... | .......... | .......... |     |
| Consensus | ---------- | ---------- | ---------- | ---------- | ---------- |     |

|          | 951        | 962 |
|----------|------------|-----|
| OCTDRS   | .......... | ..  |
| A1HAM    | fksnmplapg | hf  |
| A2BHUM   | .......... | ..  |
| A2HUM    | .......... | ..  |
| B1HUM    | .......... | ..  |
| B1TUR    | .......... | ..  |
| B2HAM    | .......... | ..  |
| B2RAT    | .......... | ..  |
| D2RAT    | .......... | ..  |
| M2RAT    | .......... | ..  |
| MDRS     | .......... | ..  |
| S1CRAT   | .......... | ..  |
| Consensus | ---------- | --  |

DNA ENCODING AN INSECT OCTOPAMINE RECEPTOR

FIELD OF THE INVENTION

The present invention pertains, in general, to invertebrate octopamine receptor proteins and to polynucleotides encoding such receptors. The present invention relates in particular, to invertebrate receptors that are recombinantly expressed in mammalian cells. The receptor proteins of the invention mediate the attenuation of adenylate cyclase activity and exhibit a pharmacological profile that is unique but closely related to mammalian adrenergic receptors.

The present invention further relates to drug screening methods for the development of specific human pharmacological drugs and insecticides targeted for the octopamine receptor system.

BACKGROUND INFORMATION

Octopamine, a biogenic amine, plays a major role as a transmitter, hormone, and neuromodulator in invertebrates (see P. D. Evans, Adv. Insect Physiol. 15:317-473 (1980), for review). Through the use of pharmacological and biochemical assays, specific receptors for octopamine have been identified in many invertebrate phyla, including arthropods and molluscs (J. A. Nathanson and P. Greengard, Science. 180:308-310 (1973); J. Axelrod and J. M. Saavedra, Nature 265:501-504 (1977); A. J. Harmer and A. S. Horn, Mol. Pharmacol. 13:512-520 (1977); R. J. Walker and G. A. Kerkut, Comp. Biochem. 61C:261-266 (1978); S. Konishi and E. A. Kravits, J. Physiol. 279:215- 229 (1978); B. Battelle and E. A. Kravits, J. Pharmacol. Exp. Ther. 205:438-448 (1978); J. A. Nathanson, Science. 203:65-68 (1979); R. P. Bodnaryk, Insect Biochem. 9:155-162 (1979); B. Battelle et al., Experientia 35:778 (1979); E. A. Kravits et al., J. Exp. Biol. 89:159-175 (1980); P. D. Evans, J. Physiol. 318:99-122 (1981) and P. D. Evans, J. Exp. Biol. 129:239-250 (1987); M. S. Livingstone et al., J. Neurobiol. 12:27-54 (1981); A. Uzzan and Y. Dudai, J. Neurochem. 38:1542-1550 (1982); R. M. Harris-Warrick and E. A. Kravitz, J. Neurosci. 4:1976-1993 (1984); P. D. Evans et al., J. Pharm. Pharmacol. 40:855-861 (1988)) . Pharmacological studies in insects have provided evidence for the existence of multiple subtypes of octopamine receptors (P. D. Evans, Insect. Physiol. 15:317-473 (1980) , P. D. Evans, J. Physiol. 318:99-122 (1981) , P. D. Evans, J. Exp. Biol. 129:239-250 (1987); P. D. Evans et al. , J. Pharm. Pharmacol. 40:855-861 (1988)). In addition, there are reports indicating that octopamine receptors, pharmacologically distinct from adrenergic and dopamine receptors, exist in the mammalian central nervous system (T. P. Hicks and H. McLennan, Brain Res. 157:402-406 (1978) , T. P. Hicks and H. McLennan, Br. J. Pharmacol. 64:485-491 (1978b); W. P. C. Dao and R. J. Walker, Experientia 36:584-585 (1980)) .

Since octopamine receptors are selectively blocked by α-adrenergic antagonists and activated by α-adrenergic agonists, there has been speculation that octopamine receptors are closely related to vertebrate adrenergic receptors (P. D. Evans, Adv. Insect Physiol. 15:317-473 (1980) , P. D. Evans, J. Physiol. 318:99-122 (1981) , P. D. Evans, J. Exp. Biol. 129:239-250 (1987); J. C. Venter et al., Biochem. Pharmacol. 38:1197-1208 (1988)). However, there have been no structural data available to evaluate this hypothesis. Studies of octopamine receptors have also been complicated by the lack of specificity of available ligands both among the octopamine receptor subtypes and between octopamine receptors and receptors for other biogenic amines.

The present inventions are products, processes and compositions that relate, at least in part, to an octopamine receptor cDNA and to the protein product encoded therein. Sequence analysis of the cDNA reveals that the octopamine receptor is a member of the adrenergic/muscarinic/opsin gene superfamily of receptors (J. C. Venter et al., Prog. Neurobiol. 30:105-169 (1988), J. C. Venter et al., Biochem. Pharmacol. 38:1197-1208 (1989)). Permanent expression of this cDNA in mammalian cells provides the opportunity to study an octopamine receptor in isolation and thus, allows for the unambiguous description of a single receptor type. It also allows for a rapid and effective assay for the rational design in testing of insecticides targeted against the receptor.

SUMMARY OF THE INVENTION

It is an object of the present invention to provide a segment of a DNA molecule which codes for a octopamine receptor protein derived from invertebrates, for example, Drosophila, and the encoded proteins. It is another object of the present invention to provide a recombinant DNA molecule comprising a vector and a DNA segment which codes for the invertebrate octopamine receptor.

It is a further object of the present invention to provide a host cell stably transformed with the recombinant DNA molecule provided by this invention in a manner allowing expression of the octopamine receptor protein.

It is another object of the present invention to provide methods for screening potential pharmaceuticals and insecticides that are reactive to octopamine receptors and other related biogenic amine receptors. Such methods include a radiolabel binding and competition displacement assay and a metabolic assay that measures agonists and antagonists of octopamine mediated attenuation of adenylate cyclase.

Various other objects and advantages of the present invention will become obvious from the drawings and the detailed description of the invention.

In one embodiment, the present invention relates to a DNA segment encoding all, or a unique portion, of an invertebrate octopamine receptor. An example of an invertebrate may be the insect, Drosophila.

In another embodiment, the present invention relates to a substantially pure form of Drosophila octopamine receptor.

In a further embodiment, the present invention relates to a recombinantly produced protein having all, or a unique portion, of the amino acid sequence given in FIG. 3.

In a further embodiment, the present invention relates to a recombinant DNA molecule comprising a DNA segment encoding all, or a unique portion, of an invertebrate octopamine receptor and a vector.

In yet a further embodiment, the present invention relates to a host cell stably transformed with the above recombinant DNA molecule in a manner allowing expression of invertebrate octopamine receptor protein encoded in the recombinant DNA molecule.

In another embodiment, the present invention relates to drug screening methods for detecting agonists and antagonists of octopamine receptors comprising the steps of contacting CHO-K1 cells that have been stably transformed and express recombinant octopamine receptor with the labeled ligand yohimbine in the presence or the absence of a specific agonist or antagonist, and measuring the amount of bound labeled ligand.

In yet another embodiment, the present invention relates to a method of screening drugs and insecticides that recognize biogenic amine receptors comprising the steps of incubating forskolin and a potential drug or insecticide in non-transfected and octopamine receptor transfected CHO-K1 cells and comparing the change in cAMP concentrations to control cells that have been incubated with forskolin alone.

The entire contents of all publications mentioned herein are hereby incorporated by reference.

BRIEF DESCRIPTION OF THE DRAWINGS

FIGS. 1A–1F shows restriction map, sequencing strategy, and nucleotide (SEQ ID NO:1) and deduced amino acid sequence (SEQ ID NO:2) of the Drosophila octopamine receptor cDNA clone.

The nucleotide sequence is numbered from the first ATG of the coding region. Selected restriction sites are shown above the diagram. In the sequencing strategy diagram at the top of the figure, each arrow represents an individual clone that was sequenced at least once. The sequence has been submitted to GenBank and assigned the accession number M26181.

Figure 1A:
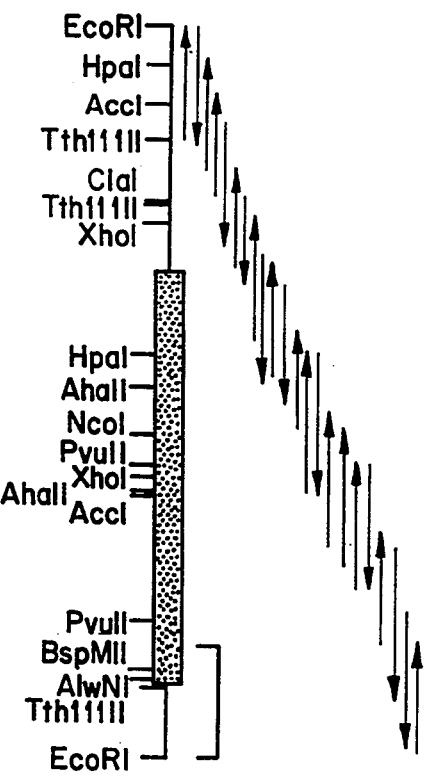
Figure 2A:
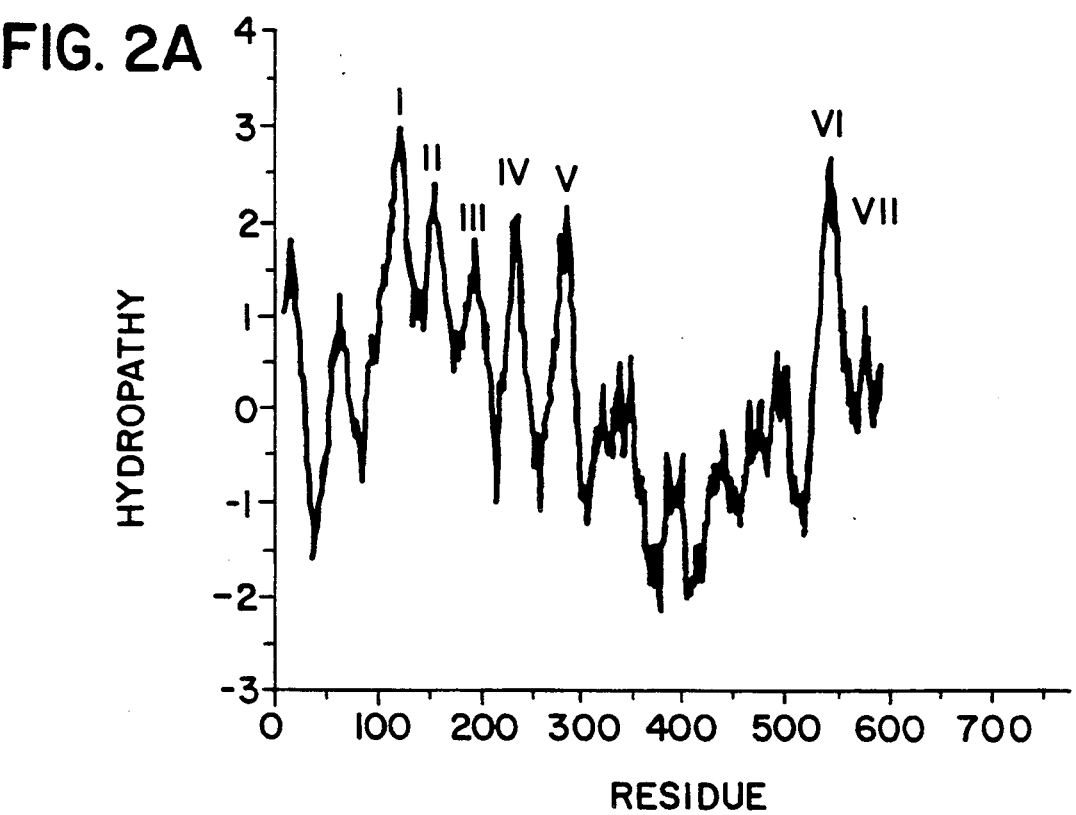
Figure 2B:
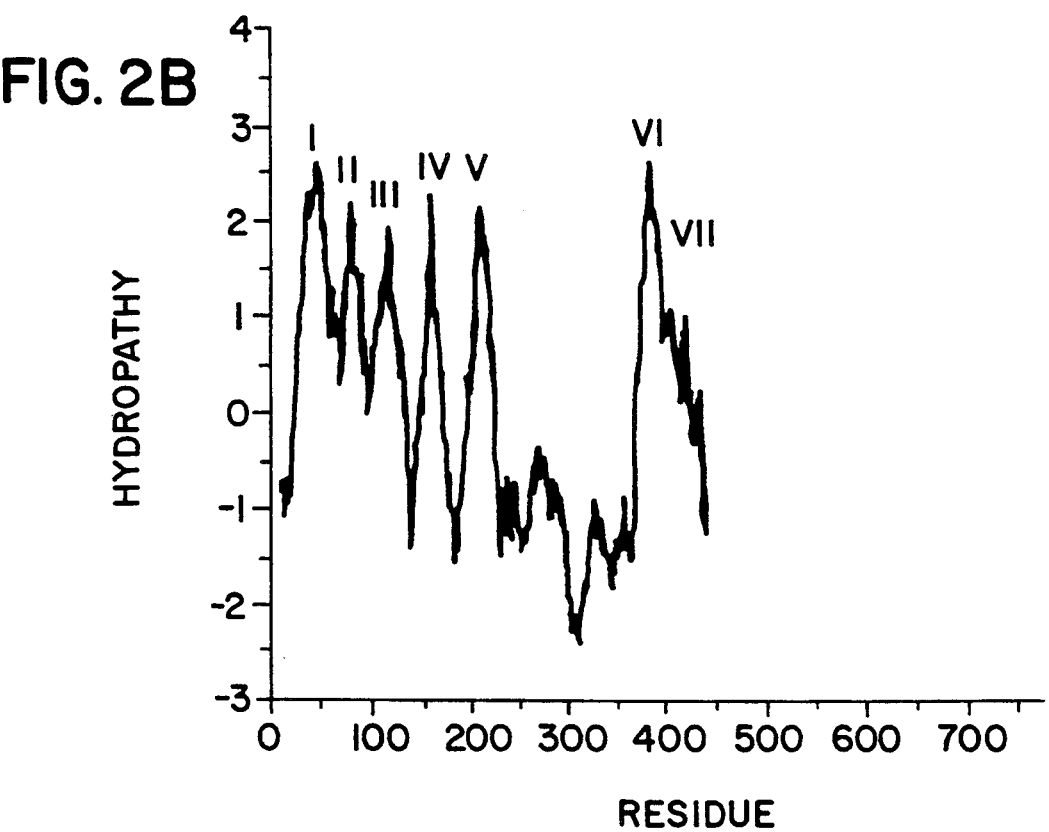

FIG. 2 shows hydropathy analysis of Drosophila octopamine, receptor and the human adrenergic receptor.

Hydropathy plots of Kyte and Doolittle (1982) were calculated using a window of 20 residues for both the Drosophila octopamine receptor and the human $\alpha_2$-adrenergic receptor (C. M. Fraser, J. Biol Chem. 264:11754–11761 (1989a)). The predicted secondary structure of both receptors contained seven stretches of hydrophobic amino acids of sufficient length to span the bilayer, similar to the secondary structure of other members of the adrenergic/muscarinic/opsin gene superfamily. The Drosophila receptor also contains additional hydrophobic residues at its amino terminus that may play a role as a putative signal sequence, a feature observed in many membrane proteins (G. Blobel and B. Dobberstein, J. Cell Biol. 67:852–862 (1975); T. Onai et al., FEBS Lett. 255:219–225 (1989)).

FIGS. 3A–3J shows a comparison of the deduced amino acid sequences of the Drosophila octopamine, receptor with other members of the gene superfamily.

Amino acid sequences were aligned using the GAP Program of the University of Wisconsin Genetics Computer Group (J. Devereux et al., Nucl. Acids Res. 12:387–395 (1984)), with gaps introduced to maximize homology followed by minor manual alignments. Conserved amino acid residues, as defined by Dayhoff et al. (1978), were considered to be identical. The amino acid sequences shown represent those of the Drosophila octopamine$_1$ receptor (Octdrs), hamster $\alpha_1$-adrenergic receptor (A1ham), human $\alpha_2$a and $\alpha_2$B-adrenergic receptors (A2hum and A2bhum), human and turkey $\beta_1$-adrenergic receptors (B1hum and B1tur), rat and hamster $\beta_2$-adrenergic receptors (B2rat and B2ham), rat D2 dopamine receptor (D2rat), rat and Drosophila muscarinic receptors (M2rat and Mdrs), and rat 5HT1c receptor (S1crat). Homology is indicated in the consensus line below the receptor sequences. Putative transmembrane regions are labeled. Conserved sites for N-linked glycosylation are indicated by an asterisk. Data are from the present study and from other works (R. Dixon et al., Nature 321:75–79 (1986); Y. Yarden et al., Proc. Natl. Acad. Sci. USA (1986); F. Z. Chung et al., FEBS Lett. 211:200–206 (1987); T. Frielle et al., Proc. Natl. Acad. USA 84:7920–7924 (1987); J. Gocayne et al., Proc. Natl. Acad. Sci. USA 84:8296–8300 (1987); S. Cotecchia et al., Proc. Natl. Acad. Sci. USA 85:7159–7163 (1988); J. W. Regan et al., Proc. Natl. Acad. Sci. USA 85:6301–6305 (1988); D. Julius et al., Science 241:558–563 (1988); T. Onai et al., FEBS Lett. 255:219–225 (1989); C. M. Fraser et al., J. Biol. Chem. 264:11754–11761 (1989a); J. R. Bunzow et al., Nature 336:783–787 (1988)) .

Figure 4:
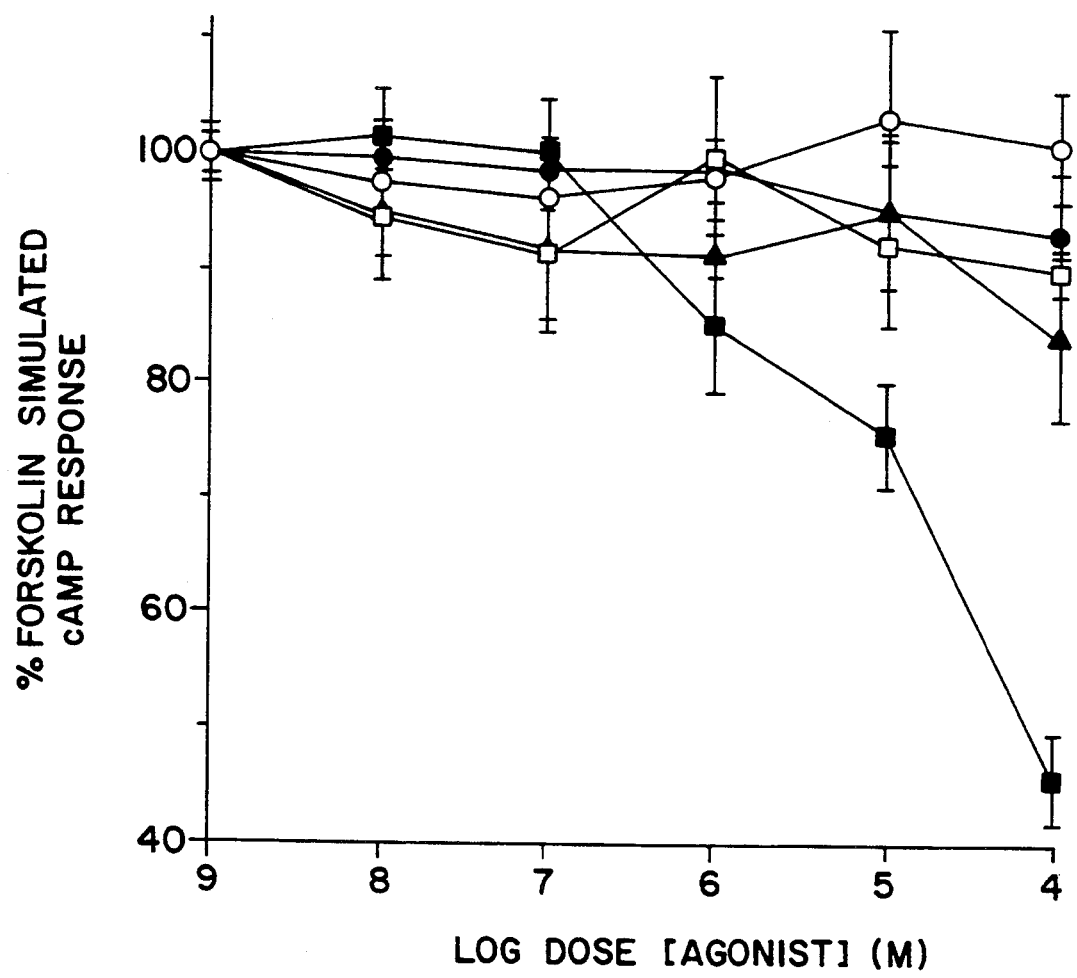

FIG. 4 shows the effect of biogenic amines on cAMP concentrations CHO-K1 cells expressing the Drosophila octopamine$_1$ receptor.

Transfected cells ($3 \times 10^5$ cells per dish) were washed once with PBS and incubated in PBS containing 1 mM 3-isobutyl-1-methylxanthine (Sigma) at 37° C. for 20 min. Agonists, at the indicated final concentrations, were added to the cultures along with 10 $\mu$M forskolin (Sigma), and cultures were incubated at 37° C. for an additional 20 min. Incubations were terminated by the addition of 6% trichloroacetic acid. Trichloroacetic acid extracts were extracted four times with distilled water-saturated ether, and cMAP concentrations were determined using a cAMP radioimmunoassay kit (New England Nuclear). Data are expressed as percent forskolin-stimulated cAMP production. In the indicated experiments, cell cultures were incubated with Bordetella pertussis islet activating protein (200 ng/ml; list biological lab) at 37° C. for 18 hr in normal culture medium prior to the assay of cAMP. Solid and open squares represent data obtained with octopamine in transfected and control cells, respectively. Solid circles represent data with epinephrine in transfected cells. Open triangles and open circles represent data with octopamine in transfected cells in the presence of 10 $\mu$M yohimbine or in cells pretreated with pertussis toxin, respectively. Data represent the average ±SEM of at least three separate experiments performed in duplicate.

FIG. 5 depicts a chromosomal and tissue localization of the Drosophila octopamine receptor. (A) Chromosomal localization of the Drosophila acotpamine, receptor. The Drosophila genomic $\lambda$ clone DGSA1641 was biotinylated using a nick translation kit (Bethesda Research Laboratories) and biotin-11-dUTP (Enzo Biochemical). The clone was detected using a DNA detection kit (Bethesda Research Laboratories) following the procedures of Engel et al. (1985). The arrow indicates the site of hybridization at 99A10-B1. (B) Drosophila genomic Southern. Eight micrograms of genomic DNA isolated from the Canton-S wild-type strain (T. Jowett, Preparation of nucleic acids. In Drosophila: A Practical Approach, D. B. Roberts, ed. (Washington, D.C.: IRL Press), pp. 275–277 (1986)) was digested with the indicated restriction enzyme (E, EcoRI, B, BamHI, and H, HindIII) and electrophoresed on a 0.6% agarose gel. Following capillary blotting, the filter was hybridized with the octopamine cDNA clone that had been $^{32}$P-labeled by the random primer method. The blot was hybridized overnight at 45° C. in 5× SSC, 0.05M sodium phosphate buffer (pH 6.8), 0.1% SDS, 5× Denhardt's, and 0.2 mg/ml denatured salmon sperm DNA. The blot was washed one time in 2× SSC, 0.1% SDS for 30 min at room temperature followed by two 30 min washed at successive temperatures (45° C., 50° C., 55° C., and 65° C.). The pattern of hybridization was the same regardless of wash temperature used in the 45° C.-65° C. range. Molecular size markers are indicated on the right of the gel. (C) Northern analysis of Drosophila heads versus bodies probed with the octopamine cDNA. RNA was prepared from 1 g of heads and 2 g of bodies using the guanidinium isothiocyanate homogenization-CsCl centrifugation procedure (J. M. Chirgwin et al., Biochemistry 18:5294–5299 (1979)). Each preparation was enriched for poly(A)+ mRNA by passing it through one Pharmacia oligo(dT) column according to the manufacturer's instructions. Approximately 8–9 μg of mRNA was added to each lane of a formaldehyde, 0.8% agarose gel. The electroblotted filter was prehybridized for 2 hr at 42° C. with 5× SSPE, 10× Denhardt's, 50% deionized formamide, 5 mg/ml denatured salmon sperm DNA and then hybridized overnight at 42° C in 5× SSPE, 1× Denhardt's, 50% formamide, 1 mg/ml denatured salmon sperm DNA, 0.1% SDS using the cDNA probe labeled with $^{32}P$ by the random primer method. The blot was washed as follows; a brief rinse in 2× SSC, 15 min in 2× SSC at room temperature, 15 min in 0.1× SSC at room temperature, and two 30 min washes in 0.1× SSC at 60° C. All washes contained 0.1% SDS.

DETAILED DESCRIPTION OF THE INVENTION

The present invention relates to segments of DNA which encode an octopamine receptor for invertebrates. In particular, the present invention relates to a DNA segment that encodes the octopamine receptor for the invertebrate, Drosophila. The DNA sequence analysis shown in FIGS. 1A–1F and amino acid sequence analysis shown in FIGS. 3A–3J demonstrate that the octopamine receptor is a member of the adrenergic/muscarinic/opsin gene superfamily of receptor.

The invention also relates to the invertebrate octopamine receptor proteins, for example, Drosophila octopamine receptors encoded by octopamine receptor DNA segments.

The octopamine protein found in invertebrates such as Drosophila has a calculated molecular weight, as determined by DNA sequence analysis of about 64,700 daltons. In another embodiment, the octopamine receptor has the amino acid sequence as set forth in FIG. 3. The amino acid sequence of the Drosophila protein receptor displays significant homology with mammalian α and β adrenergic receptors, rat and Drosophila muscarinic acetylcholine receptor and rat $D_2$ dopamine and 5HT receptors.

In another embodiment, the octopamine protein encoded by the Drosophila octopamine receptor gene is glycosylated, displaying conserved sites for N-linked glycosylation within the amino terminal domains similar to α- and β-adrenergic receptors described above. The octopamine receptor protein of the present invention is substantially free of proteins with which it is normally associated and can be bound to a solid support such as, for example, agarose, sepharose, plastic, nylon membrane or nitrocellulose paper.

The present invention also relates to a recombinant DNA molecule comprising a vector and the above-described DNA segment which encodes the invertebrate Drosophila octopamine receptor or unique portion thereof. Possible vectors include plasmids, for example, pSVL expression vector, and other vectors known in the art that either transiently or stably transform host cells in a manner which allows expression of the octopamine receptor proteins. Examples of appropriate eukaryotic cells include, for example, Chinese hamster kidney cells. Other eukaryotic cells such as Baculovirus and Schneider cells or prokaryotic expression systems could be adapted for the production of Drosophila octopamine proteins.

The present invention further relates to drug screening methods that may be useful in developing specific insecticides and human pharmaceutical drugs targeted against the octopamine receptor system. In a binding assay provided herein, octopamine receptor genes isolated from a specific DNA library are inserted into a plasmid expression vector and used to transfect a Chinese hamster kidney cell called CHO-K1 cells. These cells stably integrate the foreign DNA into the genome. Cells that express the insect octopamine receptor and process receptor into the mammalian cell membrane are cloned, expanded and frozen down for further use as membrane preparations in a ligand binding assay. In the assay disclosed herein, the membrane bound octopamine receptor preparations are incubated with labeled yohimbine, an α2-adrenergic receptor antagonist. Suitable labels include for example, radiolabels such as $^3H$. Transfected CHO-K1 cell membranes displace saturable, high affinity binding of labeled ligand yohimbine, with a calculated equilibrium dissociation constant described herein. No specific labeled ligand is observed bound to membranes prepared from control, untransfected CHO-K1 cells. The binding of potential drug agonists and antagonists to the insect octopamine receptor are examined in competition displacement studies with labeled yohimbine. Thus, in one method taught by the present invention, the membrane preparations are incubated with a fixed concentration of labeled yohimbine in the presence of increasing concentrations of either agonist or antagonist. After the incubations are terminated, the reaction mixture containing labeled ligand bound to receptor membranes is calculated by measuring label. Analogs of octopamine (agonists) display a stronger affinity for the octopamine receptor and displace labeled ligand whereas antagonist show a lower affinity for octopamine receptors and do not displace bound labeled ligand.

Another aspect of the present invention relates to another drug screening method that identifies new compounds with biogenic amine (agonists) or antagonist activity for biogenic receptors by measuring adenylate cyclase concentrations in transfected CHO-K1 cells expressing octopamine receptors. In one embodiment, potential drugs are tested for their ability to attenuate forskolin-stimulated adenylate cyclase activity. Forskolin is added to control or octopamine receptor transfected CHO-K1 cells that stimulates increased intracellular cAMP levels in transfected cells over base CHO-K1 levels. In the presence of forskolin, known concentrations of octopamine are added and the attenuation of forskolin stimulated cyclase AMP is calculated. A potential antagonist is determined by the competitive reversal of octopamine mediated attenuation of forskolin stimulated cyclic AMP accumulation when the drug is added to the assayed transfected cells. A potential agonist drug will have no effect of forskolin stimulated cyclic AMP level in either transfected or control CHO-K1 cells.

The present invention further relates to methods of isolating other neurogenic and biogenic receptors using the octopamine receptor DNA segment described in the present invention. One skilled in the art will appreciate that the invention includes methods for isolating related octopamine receptors and other biogenic amine receptors using human genomic DNA libraries and a DNA segment encoding the octopamine receptor or a unique portion thereof as a probe in known cloning and nucleotide sequencing methods. One skilled in the art will also appreciate that such related receptors could be used in the methods described above for the design of screening of incesticides and drugs.

Certain aspects of the invention are described in greater detail in the non-limiting Examples that follow.

EXAMPLES

The following materials and procedures are referred to in the Examples that follow.

Screening of a Drosophila Genomic Library

Using a human brain $\beta_2$-adrenergic receptor as a hybridization probe, a Drosophila genomic library was screened under low stringency conditions (hybridization with 30% formamide, 6× SSC, 5× Denhardt's, 50 mM NaPO$_4$ [pH 7.4], 50 µg/ml sheared salmon sperm DNA for 18 hr at 49° C.; wash with 6× SSC, 0.1% SDS for 20 min at room temperature followed by 3× SSC for 20 min at room temperature). Three λ gt11 clones were isolated, and a 367 bp BglII fragment of one of these clones was used to screen a cDNA library.

Screening of a Drosophila cDNA Library

The Drosophila head cDNA library was made from poly(A)+ mRNA isolated from the heads of the Oregon-R strain of *D. melanogaster*. A 367 bp BglII fragment of the Drosophila genomic clone (DGSA1641; see C. M. Fraser et al., J. Biol. Chem. 264:11754–11761 (1989)) was radiolabeled by random priming for screening of the Drosophila cDNA library. The library was transferred to Hybond-N filters (Amersham) and screened with the $^{32}$P-labeled probe under the following hybridization conditions; 30% formamide, 6× SSC, 5× Denhardt's 50 mM sodium phosphate (pH 7.4), 50 µg/ml sheared salmon sperm DNA at 42° C. for 18 hr. Filters were washed in 2× SSC, 0.1% SDS and then in 0.5× SSC at 55° C. for 30 min each. Seven positive clones were isolated from the 6000,000 pfu screened; 6 of these displayed identical restriction maps.

Sequence Analysis of Drosophila cDNA Clones

A 3.3 kb EcoRI cDNA insert from 1 of the 6 identical clones that hybridized on Southern blots with the DGSA1641 probe at high stringency (0.5× SSC at 55° C. for 30 min) was isolated. Blunt ends were created with Klenow fragment of DNA polymerase, and the insert was subcloned in both orientations into the HincII site in the multiple cloning region of pVZ1 (A. Henikoff and M. K. Eghtedarzadeh, Genetics 117:711–725 (1987)). Exonuclease III digestion was performed at 37° C., and aliquots were removed every 30 s as described by Henikoff (1987). Single-stranded DNA was purified and prepared for sequence analysis using an Applied Biosystems 370A Automated DNA Sequencer (J. Gocayne et al., Proc. Natl. Acad. Sci. USA 84:8296–8300 (1987)).

Expression of the Drosophila Receptor in CHO-K1 Cells

Based on analysis of open reading frames, the region of approximately 2.2 kb, as shown in FIGS. 1A–1F, was selected for expression in CHO-K1 cells. A 2.2 kb fragment as excised from pVZ1 by sequential enzyme cuts. The vector was linearized with ClaI, and blunt ends were generated with DNA polymerase. The cDNA fragment was released from the vector by cleavage with AlwNI. The AlwNI site is contained within the defined open reading frame and this necessitated reconstruction of the 5′ end of the gene with a synthetic oligonucleotide. This was accomplished by ligating the gene fragment and the following synthetic oligonucleotide:

5′-CTAGATGCCATCGGCAGATCAAAT-CAAATC-3′
3′-TACGGTAGCCGTCTAGTT-5′ into pSVL that had been cleaved with XbaI and SmaI. The synthetic oligonucleotide reconstructs the 5′ end of the gene, destroys the AlwNI site with a silent mutation, and adds a terminal XbaI site, which facilitates insertion of the fragment into the expression vector in a directional manner. The 5′ portion of the fragment reconstructed for expression was excised from pSVL and ligated into M13 to confirm the sequence of the 5′ end of the construct used for expression. pSVL containing the Drosophila receptor gene was cotransfected with pMSVneo, which contains the selective marker for G418 resistance, into CHO-K1 cells (American Type Culture Collection) using the calcium phosphate precipitation technique (C. M. Fraser et al., Proc. Natl. Acad. Sci. USA C. M. Fraser et al., J. Biol. Chem. 264:11754–11761 (1989), C. M. Fraser et al., Proc. Natl. Acad. Sci. USA 85:5478–5482 (1989)). Stable transfectants were obtained by growth of the cells in culture medium containing the antibiotic, Geneticin (G418, 500 µg/ml; GIBCO). Colonies derived from single cells were isolated and expanded as described (C. M. Fraser et al., Proc. Natl. Acad. Sci. USA 85:5478–5482 (1988), C. M. Fraser et al., J. Biol. Chem. 264:11754–11761 (1989), C. M. Fraser et al., Proc. Natl. Acad. Sci. USA 85:5478–5482 (1989)) and those transfectants expressing the Drosophila gene were identified by Northern blot analysis of total cellular RNA.

Northern Analysis of Transfected CHO-K1 Cells Expressing the Drosophila Octopamine Receptor RNA was isolated from five 150 mm plates of confluent cells using guanidinium thiocyanate according to the method of Chirgwin et al., (1979). Total RNA (20 µg) from each line of transfected cells was separated on agarose gels containing formaldehyde as described by Maniatis et al. (1982). RNA was transferred to Hybond-N membranes (Amersham) in 25 mM NaPO$_4$ buffer (pH 6.5), and the membrane was hybridized with the 3.3 kb Drosophila cDNA clone radiolabeled with [$^{32}$P]cytosine (0.5×10$^6$ cpm/ml). The Northern blot was washed with 6× SSC, 0.1% SDS for 15 min at 42° C., 2× SSC for 20 min at 42° C., 2× SSC for 30 min at 56° C., and 0.5× SSC for 30 min at 56° C.

Cell Membrane Preparation and Radioligand Binding Assays

Cell membranes from transfected cells were prepared as previously described (F.-Z. Chung et al., J. Bol. Chem. 263:4052–4055 (1988); C. M. Fraser et al., Proc. Natl. Acad. Sci. USA 85:5478–5482 (1988), C. M. Fraser et al., J. Biol. Chem. 264:11754–11761 (1989), C. M. Fraser et al., Proc. Natl. Acad. Sci. USA 85:5478–5482 (1989)). [$^3$H]Yohimbine binding assays and competition displacement experiments were performed as described for the human $\alpha_2$-adrenergic receptor (C. M. Fraser et al., J. Biol. Chem. 264:11754–11761 (1989). Ligand binding data were analyzed using the LIGAND program of Munson and Rodbard (1980).

Example 1

Octopamine Receptor Gene Cloning

The known nucleotide sequence similarities among G protein-linked receptors was exploited to search for genes related to adrenergic receptors in a Drosophila genomic library using a human brain $\beta_2$-adrenergic receptor cDNA clone (F.-Z. Chung et al., FEBS Let. 211:200–206 (1987)) as a hybridization probe. Using low stringency hybridization conditions, three λgt11 clones were isolated. Partial sequence analysis revealed that the genomic clones contained exons that, when translated, displayed high homology to the transmembrane domains of mammalian adrenergic receptor proteins. Using a 367 bp fragment of Drosophila genomic DNA (clone DGSA1641) that displayed homology with the putative sixth and seventh transmembrane domains of adrenergic receptors as a hybridization probe, a 3.3kb cDNA clone from a Drosophila head cDNA library was isolated. This same 367 bp fragment of Drosophila genomic DNA was also used to isolate an $\alpha_2$-adrenergic receptor gene from a human genomic library (C. M. Fraser et al., J. Biol. Chem. 264:11754–11761 (1989)).

Example 2

Sequencing Strategy and Protein Structure

The sequencing strategy and restriction map of the 3.3 kb Drosophila cDNA clone are shown in FIGS. 1A–1F. This strategy was based upon the generation of overlapping, unidirectional exonuclease III deletions (S. Henikoff, Meth. Enzymol. 155:156–165 (1987)). Automated DNA sequence analysis was carried out using an Applied Biosystems 370A DNA Sequencer (J. Gocayne et al., Proc. Natl. Acad. Sci. USA 84:8296–8300 (1987)). As illustrated in FIGS. 1A–1F, the nucleotide sequence of this clone contains 3335 bp and has a large open reading frame that encodes a protein of 601 amino acids with a calculated molecular mass of 64,700 daltons. This cDNA clone and genomic clone DGSA1641 (originally used as a hybridization probe) contained identical sequences.

Several features of this protein suggested that it belongs to the adrenergic/muscarinic/opsin gene superfamily. Hydropathy profiles revealed seven stretches of hydrophobic amino acids of sufficient length to span the bilayer, similar to the secondary structure of other members of the gene superfamily (FIG. 2). However, unlike other members of this gene family, the Drosophila protein contains an additional sequence of hydrophobic residues at its amino terminus. The properties of this amino-terminal hydrophobic sequence suggest that it may function as a putative signal sequence, a feature observed in many membrane proteins (G. Blobel and B. Dobberstein, J. Cell. Biol. 67:852–862 (1975)). A similar region is also seen in the putative muscarinic acetylcholine receptor from Drosophila (T. Onai et al., FEBS Lett. 255:219–225 (1989)). As shown in FIGS. 3A–3J, the deduced amino acid sequence of the Drosophila protein displays significant homology with those of mammalian $\alpha$- and $\beta$-adrenergic receptors, rat and Drosophila muscarinic acetyl-choline receptors, and rat $D_2$ dopamine and 5HT receptors (R. Dixon et al., Nature 321:75–79 (1986); Y. Yarden et al., Proc. Natl. Acad. Sci. USA 83:6795–6799 (1986); F.-Z. Chung et al., FEBS Lett. 211:200–206 (1987); T. Frielle et al., Proc. Natl. Acad. Sci. USA 84:7920–7924 (1987); J. Gocayne et al., Proc. Natl. Acad. Sci. USA 84:8296–8300 (1987); S. Cotecchia et al., Proc. Natl. Acad. Sci. USA 85:7159–7163 (1988); J. W. Regan et al., Proc. Natl. Acad. Sci. USA 85:6301–6305 (1988); D. Julius et al., J. Physiol. 318:99–122 (1988); T. Onai et al., FEBS Lett. 255:219–225 (1989); C. M. Fraser et al., J. Biol. Chem. 264:11754–11761 (1989a); J. R. Bunzow et al., Nature 336:783–787 (1988)). The Drosophila receptor exhibited highest homology with $\alpha_2$-adrenergic receptors (32% and 35% identity, increasing to 66% and 70% similarity with conserved substitutions for $\alpha_2$A and $\alpha_2$B receptors, respectively). The regions of greatest amino acid identity among these receptors reside within the putative transmembrane helices. All of these receptors display conserved sites for N-linked glycosylation within their amino-terminal domains and conserved aspartic acid residues in the second and third transmembrane helices; these have been shown by site-directed mutagenesis to be involved in agonist-induced receptor activation in $\beta$-adrenergic (F.-Z. Chung et al., J. Biol. Chem. 263:4052–4055 (1988); C. M. Fraser et al., Proc. Natl. Acad. Sci. USA 85:5478–5482 (1988)) and muscarinic acetylcholine (C. M. Fraser et al., J. Biol. Chem. 264:11754–11761 (1989)) receptors.

Example 3

Permanent Expression of the Drosophila cDNA Clone in Mammalian Cells

To prove the identity and characterize the Drosophila receptor further, 2.2 kb cDNA fragment containing the open reading frame was ligated into the expression vector pSVL and cotransfected with pMSVneo into CHO-K1 cells as previously described (F.-Z. Chung et al., J. Biol. Chem. 263:4052–4055 (1988); C. M. Fraser et al., Proc. Natl. Acad. Sci. USA 85:5478–5482 (1988)). Clonal cell lines that grew in selective medium containing Geneticin were isolated and expanded. Cell lines expressing the Drosophila cDNA fragment were identified by Northern blot analysis of total cellular RNA using the $^{32}$P-labeled Drosophila cDNA clone as a hybridization probe. Several clonal cell lines were identified that contained detectable levels of receptor-specific mRNA and one was chosen with the highest level for detailed pharmacological and biochemical studies.

Due to the sequence homology between the Drosophila cDNA clone and genes encoding mammalian $\alpha_2$-adrenergic receptors (C. M. Fraser et al., J. Biol. Chem. 264:11754–11761 (1989)), the assay was performed with [$^3$H]yohimbine, an $\alpha_2$-adrenergic receptor antagonist. Transfected CHO-K2 cell membranes displayed saturable, high-affinity binding of the radioligand [$^3$H]yohimbine, with a calculated equilibrium dissociation constant ($K_d$) of 6.2 nM and a $B_{max}$ of 1.75 pmol of receptor per mg of membrane protein (Table 1). No specific radioligand binding was observed to membranes prepared from control, untransfected CHO-K1 cells. The affinity of yohimbine for the octopamine receptor is similar to that for the human $\alpha_2$-adrenergic receptor expressed in CHO-K1 cells (3.5 nM; C. M. Fraser et al., J. Biol. Chem. 264:11754–11761 (1989)).

The binding of a series of agonists and antagonists to the Drosophila receptor was examined in competition displacement studies with [$^3$H]yohimbine (Table 1). Synephrine, the N-methylated analog of octopamine, showed the highest agonist affinity ($K_i = 10.8 \pm 2.5$ μM) for the Drosophila receptor, followed by the α-adrenergic agonist clonidine ($K_i = 21 \pm 7$ μM), octopamine ($K_i = 29 \pm 6$ μM), serotonin ($K_i = 75 \pm 18$ μM), and epinephrine ($K_i = 139 \pm 41$ μM), The β-adrenergic agonist isoproterenol and dopamine displayed low affinities for the Drosophila receptor ($K_i$s $\geq 1000$ μM). Antagonists displayed a random order of potency for inhibition of [$^3$H]yohimbine binding of chlorpromazine ($K^i = 0.18 \pm 0.006$ μM) > mianserin ($K_i = 1.2 \pm 0.3$ μM) > phentolamine ($K_i = 2.2 \pm 0.7$ μM) ≥ cyproheptadine ($K_i = 2.6 \pm 0.5$ μM) > metoclopramide ($K_i = 4.6 \pm 1.4$ μM) ≥ propranolol ($K_i = 5.3 \pm 1.6$ μM). The rank orders of potency for agonist and antagonist displacement of [$^3$H]yohimbine binding to the Drosophila receptor strongly suggested that an octopamine receptor had been cloned (Evans, Insect. Physiol. 15:317–473 (1980), P. D. Evans, J. Physiol. 318:99–122 (1981), P. D. Evans, J. Exp. Biol. 129:239–250 (1987); P. D. Evans et al., J. Pharm. Pharmacol. 40:855–861 (1988)). The significantly greater receptor affinity for yohimbine and chlorpromazine as compared with metoclopramide suggested that this was an octopamine type 1 receptor subtype (see table 1; see also Evans, Insect. Physiol. 15:317–473 (1980), P. D. Evans, J. Physiol. 318:99–122 (1981), P. D. Evans, J. Exp. Biol. 129:239–250 (1987); P. D. Evans et al., J. Pharm. Pharmacol. 40:855–861 (1988)).

(1977); A. J. Harmer and A. S. Horn, Mol. Pharmacol. 13:512–520 (1977); B. Battlee and E. A. Kravits, J. Pharmacol. Exp. Ther. 205:438–448 (1978); J. A. Nathanson, Science. 203:65–68 (1979); R. P. Bodnaryk, Insect Biochem. 9:155–162 (1979); A. Uzzan and Y. Dudai, J. Neurochem 38:1542–1550 (1982); P. D. Evans, J. Exp. Biol. 129:239–250 (1987)); however, none of the agonists listed in Table 1 produced an increase over basal levels of intracellular cAMP in transfected CHO-K1 cells. These agonists also had no effect on phosphoinositide hydrolysis in transfected cells. Because of the pharmacological and structural similarities of the Drosophila receptor to mammalian $\alpha_a$-adrenergic receptors, the ability of octopamine to attenuate forskolin-stimulated adenylate cyclase activity was tested. Addition of forskolin (10 μM) to control or transfected CHO-K1 cells produced an average 35-fold increase in intracellular cAMP levels over basal values. As shown in FIG. 4, octopamine produced a dose-dependent attenuation of forskolin-stimulated cAMP levels in transfected cells that was not observed in control cells. In the presence of forskolin plus 100 μM octopamine, cAMP levels were only 46% of those seen with forskolin alone. Octopamine-mediated attenuation of forskolin stimulated cAMP accumulation was competitively antagonized by yohimbine (FIG. 4), whereas epinephrine had no effect on forskolin-stimulated cAMP levels in either transfected or control CHO-K1 cells (FIG. 4). Furthermore, in transfected cells pretreated with *Bordetella pertussis* islet activating protein, the ability of octopamine to attenuate forskolin-stimulated cAMP levels was abolished, suggesting that this response was mediated

TABLE 1

Comparison of Affinities of Various Octopamine Receptors for Agonists and Antagonists

| | | EC$_{50}$ (M) | | |
|---|---|---|---|---|
| | $K_1$ (μM)$^a$ | Octopamine$_1$$^b$ | Octopamine$_{21}$$^b$ | Octopamine$_{28}$$^b$ |
| Agonists | | | | |
| Synephrine(±) | 10.8 ± 2.5 | | | |
| Clonidine | 21 ± 7 | 6.8 × 10$^{-10c}$ | 6.4 × 10$^{-6c}$ | 2.0 × 10$^{-5c}$ |
| Octopamine(±) | 29 ± 6 | | | |
| Serotonin | 75 ± 18 | | | |
| Epinephrine(−) | 139 ± 41 | | | |
| Dopamine | >1000 | | | |
| Isoproterenol(−) | >1000 | | | |
| Antagonists | | | | |
| Yohimbine$^d$ | 0.0062 ± 0.0004 | 2.8 × 10$^{-7c}$ | | |
| Chlorpromazine | 0.18 ± 0.06 | 2.6 × 10$^{-8c}$ | 1.6 × 10$^{-4c}$ | 7.0 × 10$^{-5c}$ |
| Mianserin | 1.2 ± 0.3 | 4.5 × 10$^{-6c}$ | 1.2 × 10$^{-6c,e}$ | 2.0 × 10$^{-5c,e}$ |
| Phentolamine | 2.2 ± 0.7 | 1.9 × 10$^{-7e}$ | | |
| Cyproheptadine | 2.6 ± 0.5 | 3.7 × 10$^{-8c}$ | 2.2 × 10$^{-6c,e}$ | 5.1 × 10$^{-5c,e}$ |
| Metoclopramide | 4.6 ± 1.4 | No effect-10$^{-6e}$ | 1.0 × 10$^{-6c,e}$ | 9.5 × 10$^{-6c,e}$ |
| Propranolol(−) | 5.3 ± 1.6 | 5.4 × 10$^{-7e}$ | 2.9 × 10$^{-4e}$ | 4.0 × 10$^{-4e}$ |

Affinities of the Drosophila octopamine receptor for agonists and antagonists. Membrane bound octopamine receptors (20 μg of protein) were incubated with 6nM ($^3$H)yolohimbine in the presence of increasing concentrations of the indicated agonists (0.1 μM to w mM) or antagonists (10 nM to 200 μM).
Incubations were performed at 37° C. for 20 min in a final volume of 250 μl and terminated by filtration over Whatman GF/C glass fiber filters. Experiments were repeated three times in triplicate, and the average inhibition constants (±SD) were calculated using the LIGAND program of Munson and Rodbard (1980).
$^a$This work.
$^b$This represents work done on a locust neuromuscular preparation.
$^c$Data from Evans (1982).
$^d$Values calculated from analysis of ($^1$H)yohimbine saturation binding isotherms (Munson and Rodbard, 1980).
$^e$Data from Evans (1981).

Example 4

Octopamine-Mediated Attenuation of Adenylate Cyclase Activity

Numerous reports have described an octopamine-sensitive adenylate cyclase system in insects (J. A. Nathanson and P. Greengard, Science. 180:308–310 (1973); J. Axelrod and J. M. Saavedra, Nature 265:501–504 through a *pertussis* toxin-sensitive G protein ( P. J. Casey and A. G. Gilman, J. Biol. Chem. 263:2577–2580 (1988); M. A. Lochrie and M. I. Simon, Biochemistry 27:4957–4965 (1988)), as is observed with the $\alpha_2$-adrenergic receptor (C. A. Fraser et al., J. Biol. Chem. 264:11754–11761 (1989)).

Example 5

Drosophila Chromosome and Tissue Localization

Figure 5A:

To determine where the octopamine receptor gene maps in the Drosophila genome, one of the genomic clones, DGSA1641, was biotinylated and hybridized to Drosophila salivary gland polytene chromosomes. As shown in FIG. 5a, the probe hybridized to a single site on the right arm of chromosome 3 at 99A10-B1. Studies are in progress to determine whether any of the known mutations that map to this site represent the octopamine receptor gene.

Figure 5B:
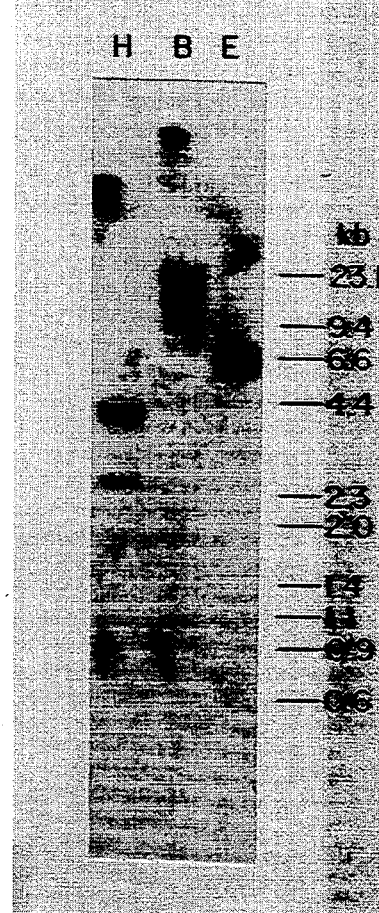

FIG. 5b shows a Drosophila genomic Southern blot probed with the octopamine receptor cDNA clone. There do not appear to be BamHI or EcoRI sites within this gene, since only single bands of 23 kb (BamHI) or 6.6 kb (EcoRI) appear in these lanes. The hybridization pattern was unchanged by washing at 45° C., 50° C., 55° C., or 65° C. Thus, under conditions used in this example DNA probe appears to be hybridizing to a single gene. This is consistent with other in situ hybridization studies, which also showed a single hybridization site. This gene does not appear to be highly polymorphic in the Canton-S wild-type strain. It remains to be determined whether lower stringency hybridization conditions can be used to isolate other pharmacologically distinct octopamine receptor genes.

Figure 5C:
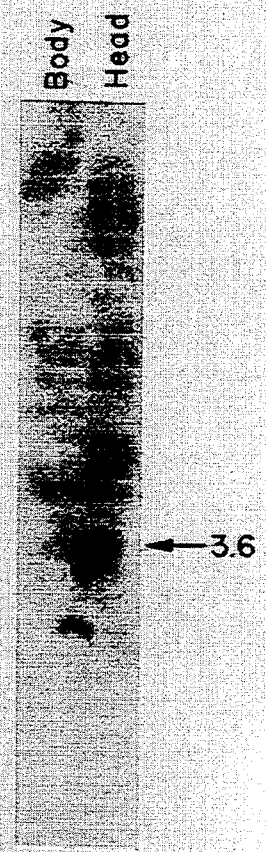

Octopamine receptors have been found in the central and peripheral nervous systems of insects (P. D. Evans, Adv. Insect Pysiol. 15:317–473 (1980)) as well as in skeletal muscle (P. D. Evans, J. Physiol. 318:99–122 (1981), P. D. Evans, J. Exp. Biol. 129:239–250 (1987); P. D. Evans et al., J. Pharm. Pharmacol. 40:855–861 (1988)). To determine whether the cloned octopamine receptor gene showed differential expression in nervous system versus skeletal muscle and gut, a comparison was made between the intensity of hybridization of $^{32}$P-labeled cDNA to equivalent amounts of poly(A)+ mRNA from Drosophila heads versus bodies. The heads are enriched in nervous system, whereas the bodies are enriched for skeletal muscle (from the flight muscles in the thorax) and for gut (in the abdomen). As shown in FIG. 5c, heads are substantially enriched for a single 3.6 kb mRNA compared with bodies. After a 7 day exposure, there is distinct hybridization in the heads, but no signal is apparent in the bodies. Control experiments using actin as a probe showed that each lane on this Northern gel had approximately the same level of mRNA. The octopamine receptor mRNA is relatively rare, since the control actin hybridization was visible after a 1 hr exposure but the same gel required a 7 day exposure to see a signal for the receptor mRNA.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. An isolated DNA segment selected from the group consisting of:
   (a) a DNA segment encoding an invertebrate octopamine receptor protein comprising the amino acid sequence set forth in Sequence ID NO:2 and
   (b) a DNA segment which is capable of hybridizing to the complement of a DNA segment according to (a) under low stringency hybridization conditions and which encodes an invertebrate octopamine receptor protein.

2. The DNA segment according to claim 1 wherein said invertebrate is an insect.

3. The DNA segment according to claim 1 wherein the invertebrate is Drosophila.

4. The DNA segment according to claim 1 wherein said DNA segment has the nucleotide sequence shown in SEQ. ID. NO:1.

5. A recombinant DNA molecule comprising
   i) said DNA segment according to claim 1; and
   ii) a vector.

6. The recombinant DNA molecule according to claim 5 wherein said vector is a plasmid, bacteriophage or eucaryotic virus vector.

7. The recombinant DNA molecule according to claim 6 wherein said vector is the plasmid expression vector pSVL.

8. A mammalian cell containing the recombinant DNA molecule of claim 7.

9. The mammalian cell according to claim 8 wherein said cell is CHO-K1 cell.

10. A host cell containing the recombinant DNA molecule according to claim 5.

11. The host cell according to claim 10 wherein said host cell is a mammalian cell.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3335 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 319..2121

( x i ) SEQUENCE DESCRIPTION: SEQ ID NO:1:

```
GAATTCGTTC TTGTGTAATA AATAAATTGC CAACAATTAT AACTTGCAGT CCACTCAGGC      60

ATATTCAAAT GAAATGTGCC ACAAAATGTT TACGGTCATT GCAACTCAAA GCGACAGACC     120

ATAGACGAGG TGCAAGGTGT TGTGGCAGTT GCAGAAAAAC TAAAAGAAAG CCGTAAGGCT     180

TGACCAAAAA TTAATAACTG ATAAAAGCAG AAATAAGTCA AAGAAGTCGG GGAAATCGCA     240

CTCAACGTCC GCCTTTCCAC CAAGACGCAT GTAAACGCAA CCGGAGCCCA AAGAAGGCAA     300

GTGGCAGGGC AGGGAAAG ATG CCA TCG GCA GAT CAG ATC CTG TTT GTA AAT     351
                    Met Pro Ser Ala Asp Gln Ile Leu Phe Val Asn
                     1               5                  10

GTC ACC ACA ACG GTG GCG GCG GCG GCT CTA ACC GCT GCG GCC GCC GTC     399
Val Thr Thr Thr Val Ala Ala Ala Ala Leu Thr Ala Ala Ala Ala Val
             15                  20                  25

AGC ACC ACA AAG TCC GGA AAC GGC AAC GCC GCA CGG GGC TAC ACG GAT     447
Ser Thr Thr Lys Ser Gly Asn Gly Asn Ala Ala Arg Gly Tyr Thr Asp
         30                  35                  40

TCG GAT GAC GAT GCG GGC ATG GGA ACG GAG GCG GTG GCT AAC ATA TCC     495
```

-continued

| | | | | | | | | | | | | | | | | |
|---|---|---|---|---|---|---|---|---|---|---|---|---|---|---|---|---|
| | Ser | Asp | Asp | Ala | Gly | Met | Gly | Thr | Glu | Ala | Val | Ala | Asn | Ile | Ser | |
| | 45 | | | | 50 | | | | | 55 | | | | | | |

| GGC | TCG | CTG | GTG | GAG | GGC | CTG | ACC | ACC | GTT | ACC | GCG | GCA | TTG | AGT | ACG | 543 |
| Gly | Ser | Leu | Val | Glu | Gly | Leu | Thr | Thr | Val | Thr | Ala | Ala | Leu | Ser | Thr | |
| 60 | | | | | 65 | | | | | 70 | | | | | 75 | |

| GCT | CAG | GCG | GAC | AAG | GAC | TCA | GCG | GGA | GAA | TGC | GAA | GGA | GCT | GTG | GAG | 591 |
| Ala | Gln | Ala | Asp | Lys | Asp | Ser | Ala | Gly | Glu | Cys | Glu | Gly | Ala | Val | Glu | |
| | | | | 80 | | | | | 85 | | | | | 90 | | |

| GAG | CTG | CAT | GCC | AGC | ATC | CTG | GGC | CTC | CAG | CTG | GCT | GTG | CCG | GAG | TGG | 639 |
| Glu | Leu | His | Ala | Ser | Ile | Leu | Gly | Leu | Gln | Leu | Ala | Val | Pro | Glu | Trp | |
| | | | | 95 | | | | | 100 | | | | | 105 | | |

| GAG | GCC | CTT | CTC | ACC | GCC | CTG | GTT | CTC | TCG | GTC | ATT | ATC | GTG | CTG | ACC | 687 |
| Glu | Ala | Leu | Leu | Thr | Ala | Leu | Val | Leu | Ser | Val | Ile | Ile | Val | Leu | Thr | |
| | | | 110 | | | | | 115 | | | | | 120 | | | |

| ATC | ATC | GGG | AAC | ATC | CTG | GTG | ATT | CTG | AGT | GTG | TTC | ACC | TAC | AAG | CCG | 735 |
| Ile | Ile | Gly | Asn | Ile | Leu | Val | Ile | Leu | Ser | Val | Phe | Thr | Tyr | Lys | Pro | |
| | | 125 | | | | | 130 | | | | | 135 | | | | |

| CTG | CGC | ATC | GTC | CAG | AAC | TTC | TTC | ATA | GTT | TCG | CTG | GCG | GTG | GCC | GAT | 783 |
| Leu | Arg | Ile | Val | Gln | Asn | Phe | Phe | Ile | Val | Ser | Leu | Ala | Val | Ala | Asp | |
| 140 | | | | | 145 | | | | | 150 | | | | | 155 | |

| CTC | ACG | GTG | GCC | CTT | CTG | GTG | CTG | CCC | TTC | AAC | GTG | GCT | TAC | TCG | ATC | 831 |
| Leu | Thr | Val | Ala | Leu | Leu | Val | Leu | Pro | Phe | Asn | Val | Ala | Tyr | Ser | Ile | |
| | | | | 160 | | | | | 165 | | | | | 170 | | |

| CTG | GGG | CGC | TGG | GAG | TTC | GGC | ATC | CAC | CTG | TGC | AAG | CTG | TGG | CTC | ACC | 879 |
| Leu | Gly | Arg | Trp | Glu | Phe | Gly | Ile | His | Leu | Cys | Lys | Leu | Trp | Leu | Thr | |
| | | | 175 | | | | | 180 | | | | | 185 | | | |

| TGC | GAC | GTG | CTG | TGC | TGC | ACT | AGC | TCC | ATC | CTG | AAC | CTG | TGT | GCC | ATA | 927 |
| Cys | Asp | Val | Leu | Cys | Cys | Thr | Ser | Ser | Ile | Leu | Asn | Leu | Cys | Ala | Ile | |
| | | | 190 | | | | | 195 | | | | | 200 | | | |

| GCC | CTC | GAC | CGG | TAC | TGG | GCC | ATT | ACG | GAC | CCC | ATC | AAC | TAT | GCC | CAG | 975 |
| Ala | Leu | Asp | Arg | Tyr | Trp | Ala | Ile | Thr | Asp | Pro | Ile | Asn | Tyr | Ala | Gln | |
| | 205 | | | | | 210 | | | | | 215 | | | | | |

| AAG | AGG | ACC | GTT | GGT | CGC | GTC | CTG | CTC | CTC | ATC | TCC | GGG | GTG | TGG | CTA | 1023 |
| Lys | Arg | Thr | Val | Gly | Arg | Val | Leu | Leu | Leu | Ile | Ser | Gly | Val | Trp | Leu | |
| 220 | | | | | 225 | | | | | 230 | | | | | 235 | |

| CTT | TCG | CTG | CTG | ATA | AGT | AGT | CCG | CCG | TTG | ATC | GGC | TGG | AAC | GAC | TGG | 1071 |
| Leu | Ser | Leu | Leu | Ile | Ser | Ser | Pro | Pro | Leu | Ile | Gly | Trp | Asn | Asp | Trp | |
| | | | | 240 | | | | | 245 | | | | | 250 | | |

| CCG | GAC | GAG | TTC | ACA | AGC | GCC | ACG | CCC | TGC | GAG | CTG | ACC | TCG | CAG | CGA | 1119 |
| Pro | Asp | Glu | Phe | Thr | Ser | Ala | Thr | Pro | Cys | Glu | Leu | Thr | Ser | Gln | Arg | |
| | | | 255 | | | | | 260 | | | | | 265 | | | |

| GGC | TAC | GTG | ATC | TAC | TCC | TCG | CTG | GGC | TCC | TTC | TTT | ATT | CCG | CTG | GCC | 1167 |
| Gly | Tyr | Val | Ile | Tyr | Ser | Ser | Leu | Gly | Ser | Phe | Phe | Ile | Pro | Leu | Ala | |
| | | | 270 | | | | | 275 | | | | | 280 | | | |

| ATC | ATG | ACG | ATC | GTC | TAC | ATC | GAG | ATC | TTC | GTG | GCC | ACG | CGG | CGC | CGC | 1215 |
| Ile | Met | Thr | Ile | Val | Tyr | Ile | Glu | Ile | Phe | Val | Ala | Thr | Arg | Arg | Arg | |
| | 285 | | | | | 290 | | | | | 295 | | | | | |

| CTA | AGG | GAG | CGA | GCC | AGG | GCC | AAC | AAG | CTT | AAC | ACG | ATC | GCT | CTG | AAG | 1263 |
| Leu | Arg | Glu | Arg | Ala | Arg | Ala | Asn | Lys | Leu | Asn | Thr | Ile | Ala | Leu | Lys | |
| 300 | | | | | 305 | | | | | 310 | | | | | 315 | |

| TCC | ACT | GAG | CTC | GAG | CCG | ATG | GCA | AAC | TCC | TCG | CCC | GTC | GCC | GCC | TCC | 1311 |
| Ser | Thr | Glu | Leu | Glu | Pro | Met | Ala | Asn | Ser | Ser | Pro | Val | Ala | Ala | Ser | |
| | | | | 320 | | | | | 325 | | | | | 330 | | |

| AAC | TCC | GGC | TCC | AAG | TCG | CGT | CTC | CTA | GCC | AGC | TGG | CTT | TGC | TGC | GGC | 1359 |
| Asn | Ser | Gly | Ser | Lys | Ser | Arg | Leu | Leu | Ala | Ser | Trp | Leu | Cys | Cys | Gly | |
| | | | 335 | | | | | 340 | | | | | 345 | | | |

| CGG | GAT | CGG | GCC | CAG | TTC | GCC | ACG | CCT | ATG | ATC | CAG | AAC | GAC | CAG | GAG | 1407 |
| Arg | Asp | Arg | Ala | Gln | Phe | Ala | Thr | Pro | Met | Ile | Gln | Asn | Asp | Gln | Glu | |
| | | 350 | | | | | 355 | | | | | 360 | | | | |

| AGC | ATC | AGC | AGT | GAA | ACC | CAC | CAG | CCG | CAG | GAT | TCC | TCC | AAA | GCG | GGT | 1455 |
| Ser | Ile | Ser | Ser | Glu | Thr | His | Gln | Pro | Gln | Asp | Ser | Ser | Lys | Ala | Gly | |
| | 365 | | | | | 370 | | | | | 375 | | | | | |

```
CCC CAT GGC AAC AGC GAT CCC CAA CAG CAG CAC GTG GTC GTG CTG GTC    1503
Pro His Gly Asn Ser Asp Pro Gln Gln Gln His Val Val Val Leu Val
380             385                 390                 395

AAG AAG TCG CGT CGC GCC AAG ACC AAG GAC TCC ATT AAG CAC GGC AAG    1551
Lys Lys Ser Arg Arg Ala Lys Thr Lys Asp Ser Ile Lys His Gly Lys
            400                 405                 410

ACC CGT GGT GGC CGC AAG TCG CAG TCC TCG TCC ACA TGC GAG CCC CAC    1599
Thr Arg Gly Gly Arg Lys Ser Gln Ser Ser Ser Thr Cys Glu Pro His
                415                 420                 425

GGC GAG CAA CAG CTC TTA CCC GCC GGC GGG GAT GGC GGT AGC TGC CAG    1647
Gly Glu Gln Gln Leu Leu Pro Ala Gly Gly Asp Gly Gly Ser Cys Gln
            430                 435                 440

CCC GGC GGA GGC CAC TCT GGA GGC GGA AAG TCG GAC GCC GAG ATC AGC    1695
Pro Gly Gly Gly His Ser Gly Gly Gly Lys Ser Asp Ala Glu Ile Ser
    445                 450                 455

ACG GAG AGC GGG AGC GAT CCC AAA GGT TGC ATA CAG GTC TGC GTG ACT    1743
Thr Glu Ser Gly Ser Asp Pro Lys Gly Cys Ile Gln Val Cys Val Thr
460             465                 470                 475

CAG GCG GAC GAG CAA ACG TCC CTA AAG CTG ACC CCG CCG CAA TCC TCG    1791
Gln Ala Asp Glu Gln Thr Ser Leu Lys Leu Thr Pro Pro Gln Ser Ser
                480                 485                 490

ACG GGA GTC GCT GCC GTT TCT GTC ACT CCG TTG CAG AAG AAG ACT AGT    1839
Thr Gly Val Ala Ala Val Ser Val Thr Pro Leu Gln Lys Lys Thr Ser
            495                 500                 505

GGG GTT AAC CAG TTC ATT GAG GAG AAA CAG AAG ATC TCG CTT TCC AAG    1887
Gly Val Asn Gln Phe Ile Glu Glu Lys Gln Lys Ile Ser Leu Ser Lys
        510                 515                 520

GAG CGG CGA GCG GCT CGC ACC CTG GGC ATC ATC ATG GGC GTG TTC GTC    1935
Glu Arg Arg Ala Ala Arg Thr Leu Gly Ile Ile Met Gly Val Phe Val
    525                 530                 535

ATC TGC TGG CTG CCC TTC TTC CTC ATG TAC GTC ATT CTG CCC TTC TGC    1983
Ile Cys Trp Leu Pro Phe Phe Leu Met Tyr Val Ile Leu Pro Phe Cys
540             545                 550                 555

CAG ACC TGC TGC CCC ACG AAC AAG TTC AAG AAC TTC ATC ACC TGG CTG    2031
Gln Thr Cys Cys Pro Thr Asn Lys Phe Lys Asn Phe Ile Thr Trp Leu
                560                 565                 570

GGC TAC ATC AAC TCG GGC CTG AAT CCG GTC ATC TAC ACC ATC TTC AAC    2079
Gly Tyr Ile Asn Ser Gly Leu Asn Pro Val Ile Tyr Thr Ile Phe Asn
            575                 580                 585

CTG GAC TAC CGC CGG GCC TTC AAG CGA CTT CTG GGC CTG AAT              2121
Leu Asp Tyr Arg Arg Ala Phe Lys Arg Leu Leu Gly Leu Asn
        590                 595                 600

TGAGGCTGGC TGGCGGGGGC GGGTGGAAGA TATAAACCGG GCCAATCATG GTTCGAGCGG   2181
GAGAGCGTAA CTCAAAGTTT GTGCCAAACT TAAATGGTCG TGTATGCGTT CAGCGGAGAT   2241
CTCAGTCTAT GTACAGTTGG ACCCCAGTT GATGAACTTC CGAGTTCAAC TTCTCTAACA    2301
CATATATACT TTCAAATGCC TTCTTGGTGA ACTCATTTTG AAGAAGTGGA TGAATTTGGT   2361
AAAGTGTAAT AGATTGAATA TAATTTTTAA TGTTAACGT TTCGGCAAAG TGAAAAGCCC    2421
CCACATTGGA AAGTCAAAGA TGAGACTCGA GTGTATATAT AGTTTCAAAC TAAGTTATTA   2481
TTTCTAGCCG TAATTAAAAT ACTTTCATTT AGTTTTGAAC ATTTTTTTAA TATATTGTTG   2541
TTTGGAATCG ATTGAGATGT ACCACCACAT TAAGCGTAGA TTGTTCAATA CTCATACTAA   2601
AATGGGTTGT GCTGCGATTA AAGTGAGGAT GTTGCCTCAA GGCACAGCTA CTAGGAAAAT   2661
CATAAAAATT ACATGGTAAA GAATTATACA TGCATTATAC TCCAGCTAAG TGGCATCCCA   2721
AACGAGAATA GCATCAAATT GAATTTAATA CAATTAAATT AAATGTTTAG GCACAAAGAA   2781
TTGTGGCAAC TTTCGTGTTT CACCCTAAGC GTATGGATAA CCAAAAAGGT GTTTGTTAAA   2841
TTAAATCTGC GCTCAAGATA TGTAAGCAAC TACTAAGCTA AATAATAACT TCCAAGAGAG   2901
```

```
AAACGTTTTC TAGGCATTAC TTTAACGATT TGTATTTATA TGTACTTTAA TTGTAGGTAA    2961

ACGATAAACC ACTATACCTA ATGTATACTT TCAAATACGC TTTGGACTAT TTGTTAAATA    3021

ATTTAACGAT TAATTGTTTT TATGGCATAG CAACTATTGT GTTGAGTGGG CAGCTTAAAG    3081

CTAGCACATC GAAACTTACT TAAGGTAGAT AAATGTTTAA CTGCACGTTA CGAAATGCAA    3141

CAGAGTTGGC GAAAGGACGT AATTCAATGG ATGTGTTAAC TCAAGTACAT GCTATATCGT    3201

AAATGTATAT CACAATTTAT GTCTTTTAAC GACGATGTAC GATAGTTTCA CTAATTATAT    3261

TGTTTAACGA GAAAGAGCGA GCAAAGCGTA AATGAAACAA ATAAAGACA  CATTCGAATT    3321

AAAGTTAGGA ATTC                                                     3335
```

( 2 ) INFORMATION FOR SEQ ID NO:2:

( i ) SEQUENCE CHARACTERISTICS:
    ( A ) LENGTH: 601 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Pro Ser Ala Asp Gln Ile Leu Phe Val Asn Val Thr Thr Thr Val
 1               5                  10                  15

Ala Ala Ala Ala Leu Thr Ala Ala Ala Val Ser Thr Thr Lys Ser
            20                  25                  30

Gly Asn Gly Asn Ala Ala Arg Gly Tyr Thr Asp Ser Asp Asp Asp Ala
            35                  40                  45

Gly Met Gly Thr Glu Ala Val Ala Asn Ile Ser Gly Ser Leu Val Glu
     50                  55                  60

Gly Leu Thr Thr Val Thr Ala Ala Leu Ser Thr Ala Gln Ala Asp Lys
 65                  70                  75                  80

Asp Ser Ala Gly Glu Cys Glu Gly Ala Val Glu Glu Leu His Ala Ser
                85                  90                  95

Ile Leu Gly Leu Gln Leu Ala Val Pro Glu Trp Glu Ala Leu Leu Thr
                100                 105                 110

Ala Leu Val Leu Ser Val Ile Ile Val Leu Thr Ile Ile Gly Asn Ile
            115                 120                 125

Leu Val Ile Leu Ser Val Phe Thr Tyr Lys Pro Leu Arg Ile Val Gln
    130                 135                 140

Asn Phe Phe Ile Val Ser Leu Ala Val Ala Asp Leu Thr Val Ala Leu
145                 150                 155                 160

Leu Val Leu Pro Phe Asn Val Ala Tyr Ser Ile Leu Gly Arg Trp Glu
                165                 170                 175

Phe Gly Ile His Leu Cys Lys Leu Trp Leu Thr Cys Asp Val Leu Cys
                180                 185                 190

Cys Thr Ser Ser Ile Leu Asn Leu Cys Ala Ile Ala Leu Asp Arg Tyr
            195                 200                 205

Trp Ala Ile Thr Asp Pro Ile Asn Tyr Ala Gln Lys Arg Thr Val Gly
    210                 215                 220

Arg Val Leu Leu Leu Ile Ser Gly Val Trp Leu Leu Ser Leu Leu Ile    225
    230                 235                 240

Ser Ser Pro Pro Leu Ile Gly Trp Asn Asp Trp Pro Asp Glu Phe Thr
                245                 250                 255

Ser Ala Thr Pro Cys Glu Leu Thr Ser Gln Arg Gly Tyr Val Ile Tyr
            260                 265                 270

Ser Ser Leu Gly Ser Phe Phe Ile Pro Leu Ala Ile Met Thr Ile Val
    275                 280                 285
```

```
Tyr Ile Glu Ile Phe Val Ala Thr Arg Arg Arg Leu Arg Glu Arg Ala
    290             295                 300

Arg Ala Asn Lys Leu Asn Thr Ile Ala Leu Lys Ser Thr Glu Leu Glu   305
        310             315                 320

Pro Met Ala Asn Ser Ser Pro Val Ala Ala Ser Asn Ser Gly Ser Lys
                325             330                 335

Ser Arg Leu Leu Ala Ser Trp Leu Cys Cys Gly Arg Asp Arg Ala Gln
            340             345                 350

Phe Ala Thr Pro Met Ile Gln Asn Asp Gln Glu Ser Ile Ser Ser Glu
        355             360                 365

Thr His Gln Pro Gln Asp Ser Ser Lys Ala Gly Pro His Gly Asn Ser
    370             375                 380

Asp Pro Gln Gln Gln His Val Val Val Leu Val Lys Lys Ser Arg Arg
385                 390             395                 400

Ala Lys Thr Lys Asp Ser Ile Lys His Gly Lys Thr Arg Gly Gly Arg
                405             410                 415

Lys Ser Gln Ser Ser Ser Thr Cys Glu Pro His Gly Glu Gln Gln Leu
            420             425                 430

Leu Pro Ala Gly Gly Asp Gly Gly Ser Cys Gln Pro Gly Gly Gly His
        435             440                 445

Ser Gly Gly Gly Lys Ser Asp Ala Glu Ile Ser Thr Glu Ser Gly Ser
    450             455                 460

Asp Pro Lys Gly Cys Ile Gln Val Cys Val Thr Gln Ala Asp Glu Gln  465
            470             475                 480

Thr Ser Leu Lys Leu Thr Pro Pro Gln Ser Ser Thr Gly Val Ala Ala
                485             490                 495

Val Ser Val Thr Pro Leu Gln Lys Lys Thr Ser Gly Val Asn Gln Phe
            500             505                 510

Ile Glu Glu Lys Gln Lys Ile Ser Leu Ser Lys Glu Arg Arg Ala Ala
        515             520                 525

Arg Thr Leu Gly Ile Ile Met Gly Val Phe Val Ile Cys Trp Leu Pro
    530             535                 540

Phe Phe Leu Met Tyr Val Ile Leu Pro Phe Cys Gln Thr Cys Cys Pro  545
        550             555                 560

Thr Asn Lys Phe Lys Asn Phe Ile Thr Trp Leu Gly Tyr Ile Asn Ser
                565             570                 575

Gly Leu Asn Pro Val Ile Tyr Thr Ile Phe Asn Leu Asp Tyr Arg Arg
            580             585                 590

Ala Phe Lys Arg Leu Leu Gly Leu Asn
        595             600
```